US012623014B2

(12) United States Patent
Parvaneh

(10) Patent No.: US 12,623,014 B2
(45) Date of Patent: May 12, 2026

(54) SMART CONNECTOR FOR CONNECTING PATIENT TO MEDICAL PRODUCT

(71) Applicant: KONINKLIJKE PHILIPS N.V., Eindhoven (NL)

(72) Inventor: Saman Parvaneh, Danvers, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 963 days.

(21) Appl. No.: 17/790,205

(22) PCT Filed: Dec. 30, 2020

(86) PCT No.: PCT/EP2020/088008
§ 371 (c)(1),
(2) Date: Jun. 30, 2022

(87) PCT Pub. No.: WO2021/136795
PCT Pub. Date: Sep. 8, 2021

(65) Prior Publication Data
US 2023/0084777 A1 Mar. 16, 2023

Related U.S. Application Data

(60) Provisional application No. 62/955,919, filed on Dec. 31, 2019.

(30) Foreign Application Priority Data

Jan. 15, 2020 (EP) ..................................... 20151950

(51) Int. Cl.
*A61M 1/36* (2006.01)

(52) U.S. Cl.
CPC ..... *A61M 1/3656* (2014.02); *A61B 2562/225* (2013.01)

(58) Field of Classification Search
CPC ................ A61M 1/3656; A61M 39/10; A61M 2039/1005; A61M 2039/1022;
(Continued)

(56) References Cited

U.S. PATENT DOCUMENTS 11,744,654 B2 9/2023 Rohr
2008/0264413 A1 10/2008 Doherty
(Continued)

FOREIGN PATENT DOCUMENTS

WO 2017184801 A1 10/2017

OTHER PUBLICATIONS

International Search Report Dated Feb. 11, 2021 For International Application No. PCT/EP2020/088008 Filed Dec. 30, 2020.

*Primary Examiner* — Kami A Bosworth

(57) ABSTRACT

Various smart medical connection embodiments of the present disclosure encompass a magnetic connectivity manager energizing ferromagnet(s) in response to a powering on the magnetic connectivity manager and a sensing of a connection strain on a medical base (21) and/or a patient base (31) of the device, whereby a magnetic connectivity interface (22, 32) activates a magnetic connectivity between metallic module(s) and the ferromagnet(s) for interfacing the conduit channels of the bases. The various smart medical connection embodiments of the present disclosure further encompass the magnetic connectivity manager deenergizing the ferromagnet(s) in response to a powering down of the magnetic connectivity manager and/or a sensing of a disconnection strain on the base(s), whereby the magnetic connectivity interface (22, 32) deactivates the magnetic connectivity between the metallic module(s) and the ferromagnet(s) for interfacing the conduit channels of the bases.

20 Claims, 14 Drawing Sheets

(58) Field of Classification Search
CPC ...... A61M 2039/1027; A61M 2205/14; A61B
2560/0276; A61B 2562/225
See application file for complete search history.

(56) References Cited

U.S. PATENT DOCUMENTS

| | | |
|---|---|---|
| 2010/0151785 A1 | 6/2010 | Steeger |
| 2014/0213962 A1 | 7/2014 | Marterstock |
| 2017/0164846 A1 | 6/2017 | Radman |

SMART CONNECTOR FOR CONNECTING PATIENT TO MEDICAL PRODUCT

CROSS-REFERENCE TO PRIOR APPLICATIONS

This application is the U.S. National Phase application under 35 U.S.C. § 371 of International Application No. PCT/EP2020/088008, filed on Dec. 30, 2020, which claims the benefit of European Application No. 20151950.1 filed on Jan. 15, 2020 and U.S. Provisional application Ser. No. 62/955,919 filed Dec. 31, 2019. These applications are hereby incorporated by reference herein.

FIELD OF THE INVENTION

The present disclosure generally relates to connecting a patient to a medical product (e.g., a medical fluid bag or a medical equipment). The present disclosure specifically relates to a smart connector for a disconnection of a connection of a patient to a medical product due to excessive strain/force on the connection or due to a request by care team (e.g., in case of emergency).

BACKGROUND OF THE INVENTION

Pulling out a basic connector as known in the art of the present disclosure (e.g., IV line connectors and electrical connectors) between IV bag/medical equipment and a patient due to excessive strain/force on the connector may be dangerous for the patient. For example, pulling an IV line due to pain-related body movements or the patient falling may remove the IV line from the patient and causes complication such as, for example, bleeding and disconnection of important medications. Disconnection of electrical connectors, such as, for example, cables that connect a patient to a monitoring system may interrupt patient monitoring and also lead to an unnecessary alarm, such as, for example, a disconnection alarm. Furthermore, pulling a medical device, IV bag, and IV stand due to pulling connectors is another problem that may be dangerous for a patient.

Current connectors in medical facilities are simple and do not incorporate mechanisms for disconnection of a connection of a patient to a medical product due to excessive strain/force on the connection.

SUMMARY OF THE INVENTION

The present disclosure describes smart medical connections between a patient and a medical product (e.g., a medical fluid container (IV bag) or a medical equipment (bedside vital sign monitor)) that is applicable to numerous and various medical applications.

The smart medical connections of the present disclosure involve a sensing of a potentially harmful strain on a connection between a patient and a medical product, and further involves an automatic disconnecting of the patient from the medical product due to the sensed potentially harmful strain to thereby impede, hopefully prevent, any harm to patient. Additionally, the smart medical connections of the present disclosure may involve notifications to a clinical team on any disconnecting of patient of the patient from the medical product. Further, the smart medical connections of the present disclosure may involve a request by a clinician or a nurse to disconnect the patient from the medical product, such as, for example, in case of patient transfer or patient emergency care (e.g., providing electric shock to the patient).

The present disclosure may be embodied as:

(1) a smart medical connector of the present disclosure;

(2) a smart medical connection system incorporating the smart medical connector of the present disclosure; and (3) a smart medical connecting method utilizing the smart medical connector of the present disclosure.

Various embodiments of a smart medical connector of the present disclosure encompass a medical base, a patient base, a magnetic connectivity interface and a magnetic connectivity manager.

The medical base has a medical conduit channel, and the patient base has a patient conduit channel.

The magnetic connectivity interface includes one or more metallic modules and one or more ferromagnets distributively adjoined to the medical base and the patient base.

The magnetic connectivity manager includes a power supply, a ferromagnetic driver and one or more strain sensors collectively adjoined to one of the medical base or the patient base, or distributively adjoined to the medical base and the patient base.

In operation, the smart medical controller controllably energizes the ferromagnet(s) in response to a sensing by the strain sensor(s) of a connection strain on the medical base and/or the patient base. In response to an energizing of the ferromagnet(s), the magnetic connectivity interface activates a magnetic connectivity between the metallic module(s) and the ferromagnet(s) for interfacing the medical conduit channel and the patient conduit channel.

Alternatively in operation, the magnetic connectivity manager controllably deenergizes the ferromagnet(s) in response to a sensing by the strain sensor(s) of a disconnection strain on the medical base and/or the patient base. In response to a deenergizing of the ferromagnet(s), the magnetic connectivity interface deactivates the magnetic connectivity between the metallic module(s) and the ferromagnet(s) for interfacing the medical conduit channel and the patient conduit channel.

Various embodiments of a smart medical connection system of the present disclosure encompass a smart medical connector of the present disclosure, and either a medical fluid container (e.g., an IV bag) in fluid communication/communicable with the medical conduit channel via a medical fluid conduit or medical equipment (e.g., bedside vital sign monitor) in electrical communication/communicable with the medical conduit channel via the medical electrical conduit.

Various embodiments of a smart medical connecting method of the present disclosure encompass an operation a smart medical connector involving an energizing of ferromagnet(s) in response to a powering on of the smart medical connector and further in response to a sensing of a connection strain on a medical base and/or a patient base. In response to an energizing of the ferromagnet(s), the magnetic connectivity interface activates a magnetic connectivity between metallic module(s) and the ferromagnet(s) for interfacing a medical conduit channel and a patient conduit channel.

The operation a smart medical connector further involves deenergizing the ferromagnet(s) in response to either a powering down of the smart medical connector or a sensing of a disconnection strain on the medical base and/or the patient base. In response to a deenergizing of the ferromagnet(s), the magnetic connectivity interface deactivates the magnetic connectivity between the metallic module(s) and the ferromagnet(s) for interfacing the medical conduit channel and the patient conduit channel.

For purposes of the description and claims of the present disclosure:

(1) terms of the art including, but not limited to, "medical", "patient", "base", "conduit", "channel", "magnetic", "connectivity", "interface", "metallic, "module", "ferromagnet", "connectivity", "pose", "power supply", "driver" and "strain sensor" are to be interpreted as known in the art of the present disclosure and as exemplary described in the present disclosure;

(2) more particularly, the term "medical base" broadly encompasses any object serving as a basis of a connection of a smart medical connector of the present disclosure to a medical fluid container or medical equipment;

(3) more particularly, the term "medical conduit channel" broadly encompasses any channel extending through a medical base and serving as a passage for fluid, electric signals and/or optical signals through the medical base;

(4) more particularly, the term "patient base" broadly encompasses any object serving as a basis of a connection of a smart medical connector of the present disclosure to a patient;

(5) more particularly, the term "patient conduit channel" broadly encompasses any channel extending through a patient base and serving as a passage for fluid, electric signals and/or optical signals through the patient base;

(6) more particularly, the term "metallic module" broadly encompasses any object consisting of one or more metals;

(7) more particularly, the term "magnetic connectivity" broadly encompasses any magnetic attraction between metallic module(s) and ferromagnet(s);

(8) more particularly, the phrase "for interfacing the medical conduit channel and the patient conduit channel" broadly encompasses any alignment of a medical conduit channel and a patient conduit channel established and/or sustained by a magnetic connectivity between metallic module(s) and ferromagnet(s) that enables transfer of fluid, electric signals and/or optical signals from one channel to the other channel;

(9) more particularly, the term "connection strain" broadly encompasses any level of strain applied to the medical base and/or the patient base designated within a magnetic connectivity manager of the present disclosure as unharmful to the patient and/or the medical fluid container/medical equipment;

(10) more particularly, the term "disconnection strain" broadly encompasses any level of strain applied to the medical base and/or the patient base designated within a magnetic connectivity manager of the present disclosure as potentially harmful to the patient and/or the medical fluid container/medical equipment;

(11) the term "adjoined" and any tenses thereof broadly means any type of integration, attaching, mounting, coupling, etc. of objects;

(12) the term "controller" broadly encompasses all structural configurations, as understood in the art of the present disclosure and as exemplary described in the present disclosure, having a circuit board and/or an integrated circuit for controlling an application of various principles of the present disclosure for implementing a smart medical connecting method of the present disclosure;

(13) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application associated with a smart medical connecting method of the present disclosure; and

(14) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

The present disclosure will present in detail the following description of exemplary embodiments with reference to the following figures wherein:

FIGS. 8A-9B illustrate exemplary embodiments of a magnetic connectivity manager in accordance with the present disclosure;

DETAILED DESCRIPTION OF THE PREFERRED EMBODIMENTS

Figure 1A:
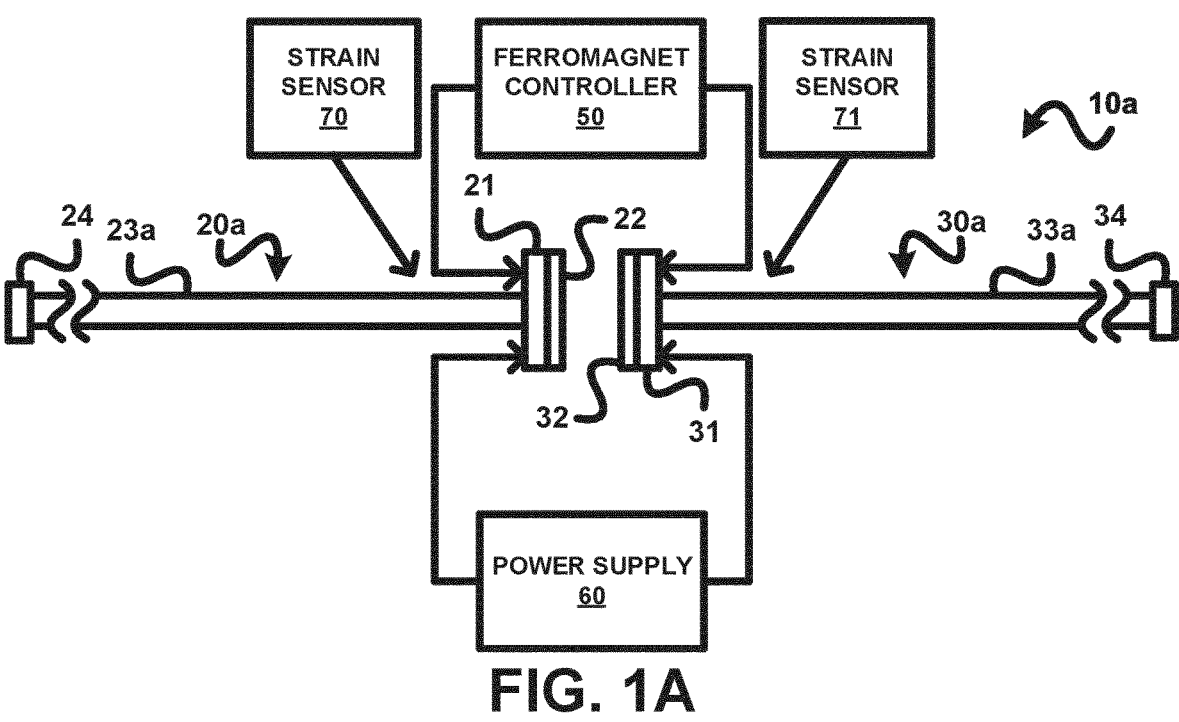
FIGS. 1A-1D illustrate exemplary embodiments of a smart medical connector in accordance with the present disclosure.

The present disclosure is applicable to numerous and various connections between patients and medical products for any medical purpose.

Examples of medical products include, but are not limited to, medical fluid containers and medical equipment.

Example of medical fluid containers include, but are not limited, crystalloid IV bags, colloid IV bags and feeding tube containers.

Example of medical equipment include, but are not limited to, electrocardiogram monitors, ventilators, blood pressure monitors, intracranial pressure monitors and ventriculostomy devices.

The present disclosure improves upon the prior art by providing smart mechanisms/processes for disconnecting a connection of a patient to a medical product due to excessive strain/force on the connection.

To facilitate an understanding of the present disclosure, the following description of FIGS. 1A-1D teaches exemplary embodiments of a smart medical connector in accordance with the present disclosure. From the description of FIGS. 1A-1D, those having ordinary skill in the art of the present disclosure will appreciate how to apply the present disclosure to make and use additional embodiments of smart medical connectors in accordance with the present disclosure.

FIGS. 1A-1D illustrate four (4) embodiments of a smart medical connector 10a-10d, each having a medical product domain 20 and a patient domain 30.

Common to all smart medical connectors 10a-10d are a medical base 21, a patient base 31, a magnetic connectivity interface 22/32, a ferromagnetic controller 50, a power supply 60. Additionally, each smart medical connectors 10a-10d employ either a medical strain sensor 70 and/or a patient strain sensor 71.

Referring to FIG. 1A, medical product domain 20a of smart medical connector 10a includes a medical conduit 23a permanently adjoined to the medical base 31, and patient domain 30a of smart medical connector 10a includes a patient conduit 33a permanently adjoined to the patient base 31 as will be further described in the present disclosure.

In practice, medical conduit 23a may have a connection element 24 (e.g., a socket, a plug, a coupler, an adapter, etc.) for connection to one or more types of medical products, and patient conduit 33a may have a connection element 34 (e.g., a socket, a plug, a coupler, an adapter, etc.) to a patient.

In one exemplary embodiment, medical conduit 23a and patient conduit 33a are fluid tubes for facilitating fluid communication between a medical fluid container (e.g., an IV bag) and a patient.

In a second exemplary embodiment, medical conduit 23a and patient conduit 33a are electric/optical cables for facilitating signal communication between the medical equipment (e.g., a monitor) and the patient.

Figure 1B:
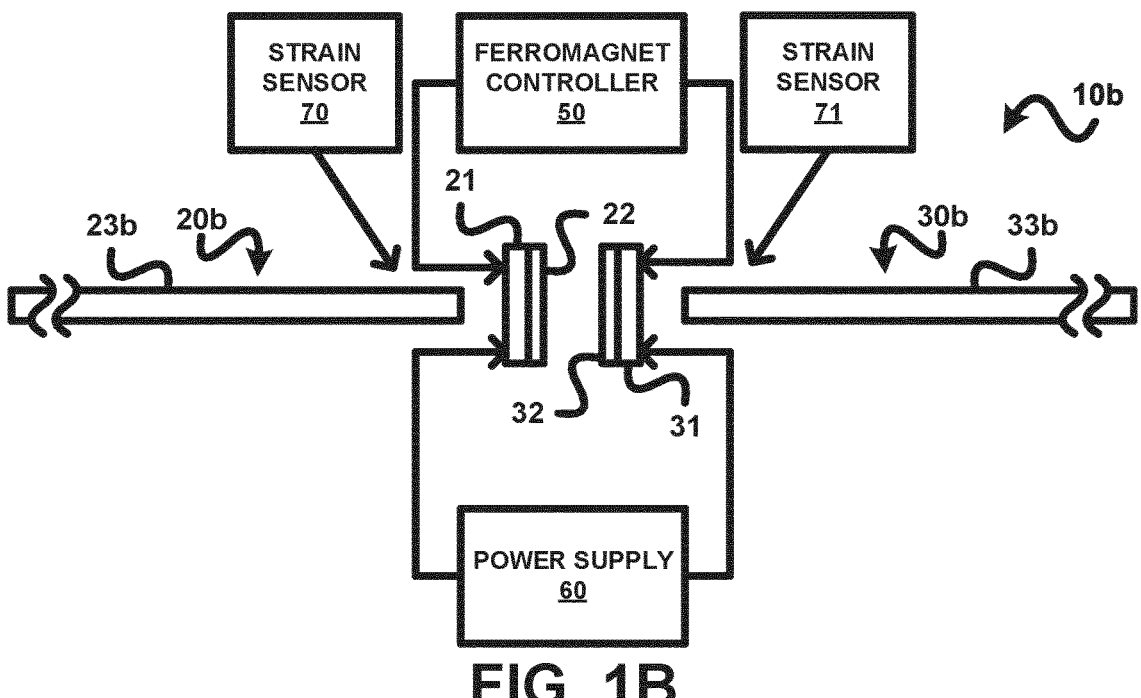

Referring to FIG. 1B, medical product domain 20b of smart medical connector 10b includes a medical conduit 23b temporarily adjoinable to the medical base 31, and patient domain 30a of smart medical connector 10a includes a patient conduit 33b temporarily adjoinable to the patient base 31 as will be further described in the present disclosure.

In practice, medical conduit 23b is a conduit extending from a medical product to be adjoined to medical base 21, and patient conduit 33b extending from a patient to be adjoined to patient base 31.

In one exemplary embodiment, medical conduit 23b and patient conduit 33b are fluid tubes for facilitating fluid communication between a medical fluid container (e.g., an IV bag) and a patient.

In a second exemplary embodiment, medical conduit 23b and patient conduit 33b are electric/optical cables for facilitating signal communication between a medical equipment (e.g., a monitor) and a patient.

Figure 1C:
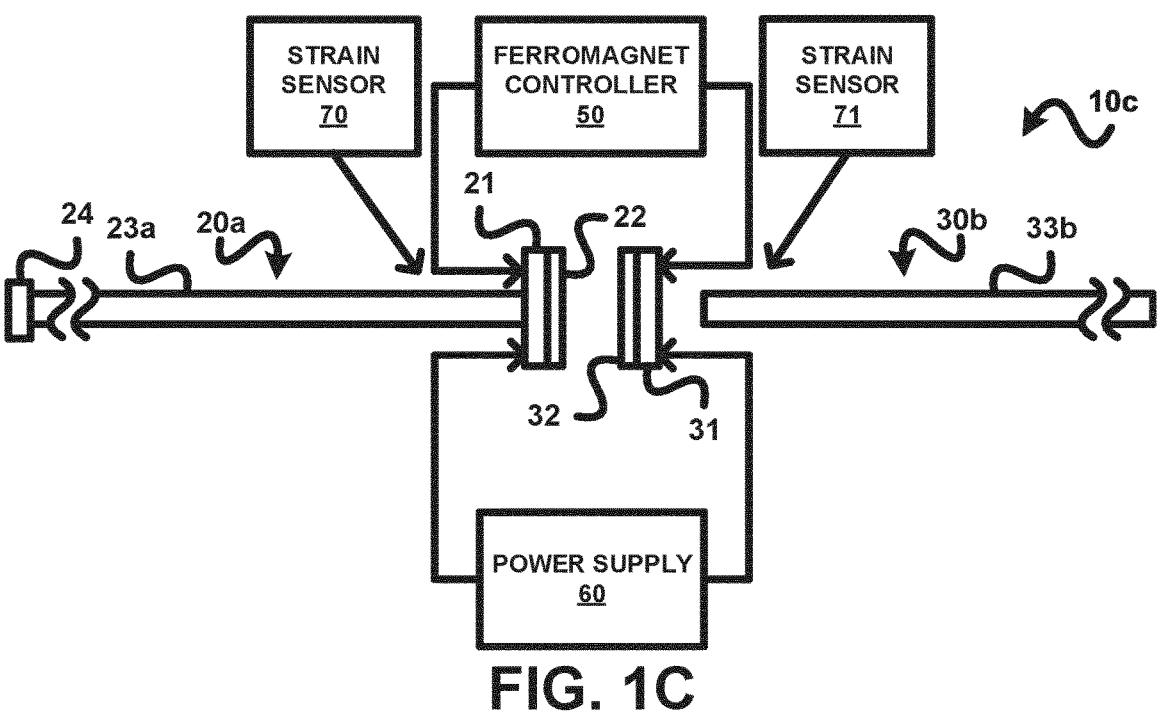

Referring to FIG. 1C, medical product domain 20c of smart medical connector 10c includes medical conduit 23a of FIG. 1A, and patient domain 30c of smart medical connector 10c includes patient conduit 33b of FIG. 1B.

Figure 1D:
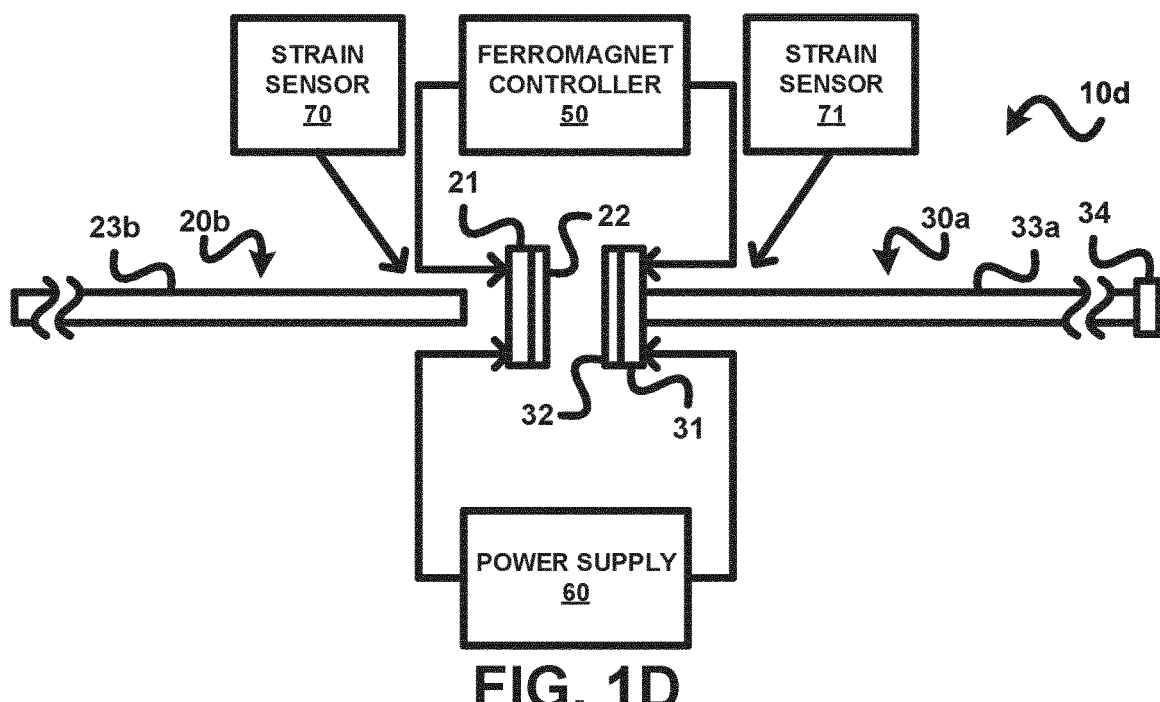

Referring to FIG. 1D, medical product domain 20d of smart medical connector 10d includes medical conduit 23b of FIG. 1B, and patient domain 30d of smart medical connector 10d includes patient conduit 33a of FIG. 1A.

In practice, a selection of one of the smart medical connectors 10a-10d for a particular medical application may be dependent upon user preference and particular type of medical product being utilized.

Referring back FIGS. 1A-1D, in practice, magnetic connectivity interface 22/32 includes one or more metallic modules and one or more ferromagnets distributively adjoined (e.g., integrated, attached, mounted, coupled, etc.) between medical base 21 and patient base 31.

Figure 2A:
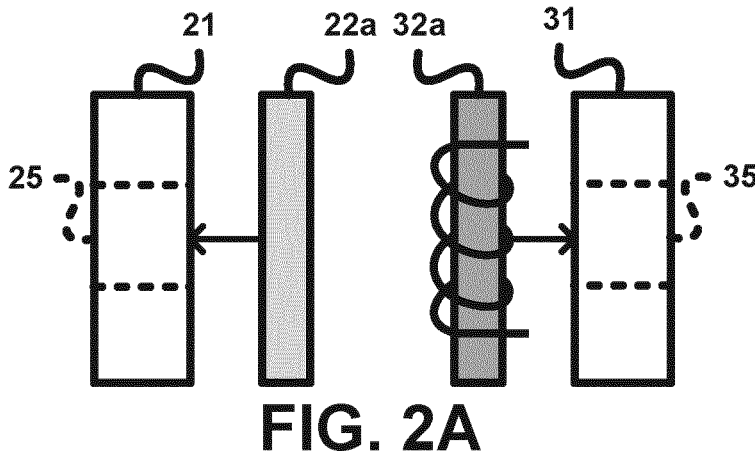
FIGS. 2A-2C illustrate exemplary embodiments of a magnetic connectivity interface in accordance with the present disclosure.

In one exemplary embodiment as shown in FIG. 2A, a metallic module 22a is adjoined to medical base 21 and a ferromagnet 32a is adjoined to patient base 31, whereby an energizing of ferromagnet 33a establishes a magnet attraction of metallic module 22a to ferromagnet 32a for establishing and/or sustaining an alignment of a medical conduit channel 25 of medical base 21 and a patient conduit channel 35 of patient base 31 as will be further described in the present disclosure.

Figure 2B:
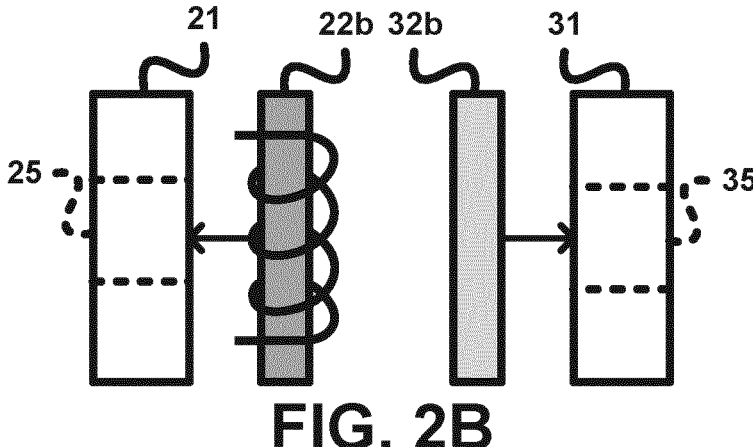

In a second exemplary embodiment as shown in FIG. 2B, a ferromagnet 22b is adjoined to medical base 21 and a metallic module 32b is adjoined to patient base 31, whereby an energizing of ferromagnet 22b establishes a magnet attraction of metallic module 32b to ferromagnet 22b for establishing and/or sustaining an alignment of medical conduit channel 25 of medical base 21 and patient conduit channel 35 of patient base 31 as will be further described in the present disclosure.

Figure 2C:
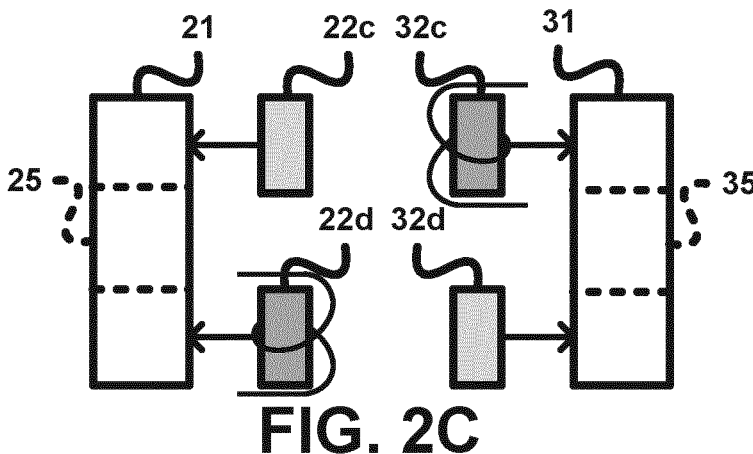

In a third exemplary embodiment as shown in FIG. 2C, a metallic module 22c and a ferromagnet 22d are adjoined to medical base 21, and a ferromagnet 32c and a metallic module 32d are adjoined to patient base 31, whereby an energizing of ferromagnet 22d establishes a magnet attraction of metallic module 32d to ferromagnet 22d and/or an energizing of ferromagnet 32c establishes a magnet attraction of metallic module 22c to ferromagnet 32c for establishing and/or sustaining an alignment of medical conduit channel 25 of medical base 21 and patient conduit channel 35 of patient base 31 as will be further described in the present disclosure.

Figure 3A:
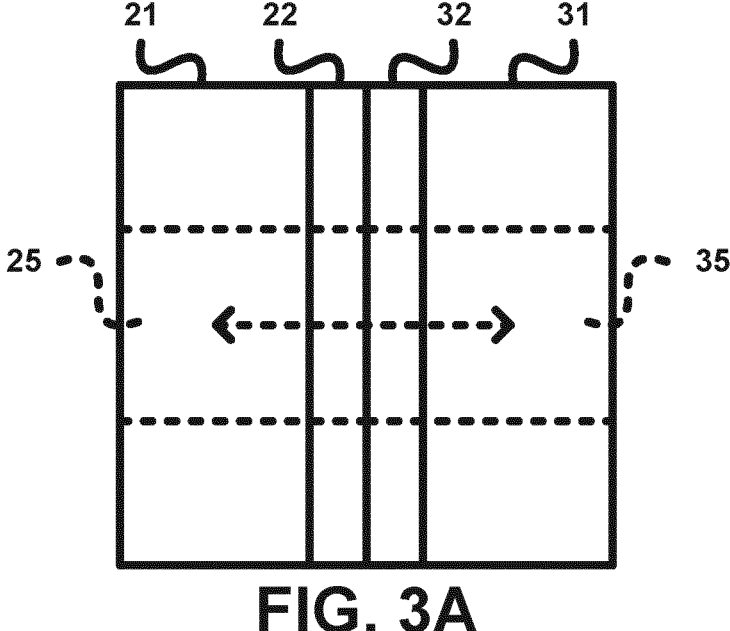
FIGS. 3A-5B illustrate exemplary embodiments of a medical base and a patient base in accordance with the present disclosure.

More particularly to an alignment of medical conduit channel 25 of medical base 21 and patient conduit channel 35 of patient base 31, FIG. 3A illustrates one exemplary embodiment of magnetic connectivity interface 22/23 being exteriorly mounted to medical base 21 and patient base 31, respectively, and an activation of magnetic connectivity interface 22/23 aligning medical conduit channel 25 of medical base 21 and patient conduit channel 35 of patient base 31 whereby fluid, electric signals and/or optical signals may be communicated via channels 25 and 35 between conduits connected to a medical product and a patient.

Figure 3B:
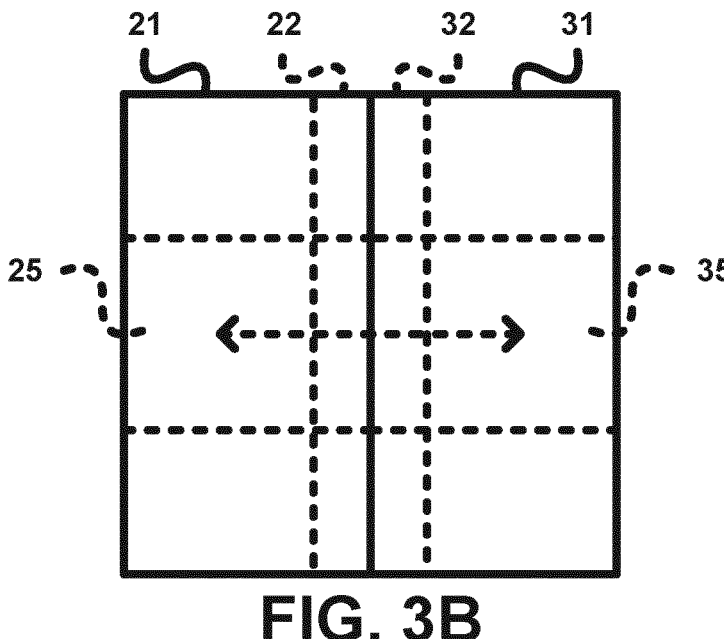

FIG. 3B illustrates one exemplary embodiment of magnetic connectivity interface 22/23 being interiorly integrated within medical base 21 and patient base 31, respectively, and an activation of magnetic connectivity interface 22/23 aligning medical conduit channel 25 of medical base 21 and patient conduit channel 35 of patient base 31 whereby fluid, electric signals and/or optical signals may be communicated via channels 25 and 35 between conduits connected to a medical product and a patient.

Figure 4A:
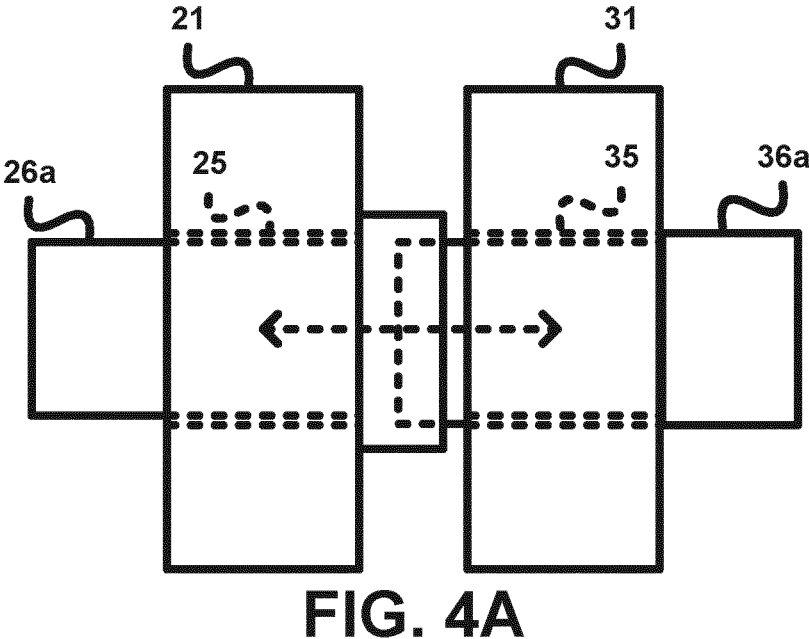

In one fluid exemplary embodiment of FIG. 3A, FIG. 4A illustrates a medical base 21 having a medical conduit segment 26a extending through medical conduit channel 25 and a patient base 31 having a patient conduit segment 36a extending through patient conduit channel 35 whereby a distal end of medical conduit segment 26a receives a distal end of patient conduit segment 36a to establish the alignment of medical conduit channel 25 of medical base 21 and patient conduit channel 35 of patient base 31 whereby fluid may be transferred via channels 25 and 35 between tubes connected to a medical product and a patient.

For FIG. 4A, medical conduit segment 26a may represent a fluid tube from a medical fluid container (e.g., IV bag), or a friction fit or a clamping coupler/adapter to a fluid tube of a medical fluid container.

For FIG. 4A, patient conduit segment 36a may represent a fluid tube from a patient, or a friction fit or clamping coupler/adapter to a fluid tube of a patient.

An activation of magnetic connectivity interface (not shown for clarity) sustains the alignment of medical conduit channel 25 of medical base 21 and patient conduit channel 35 of patient base 31, whereby fluid may be transferred via channels 25 and 35 between tubes connected to a medical product and a patient.

Figure 4B:
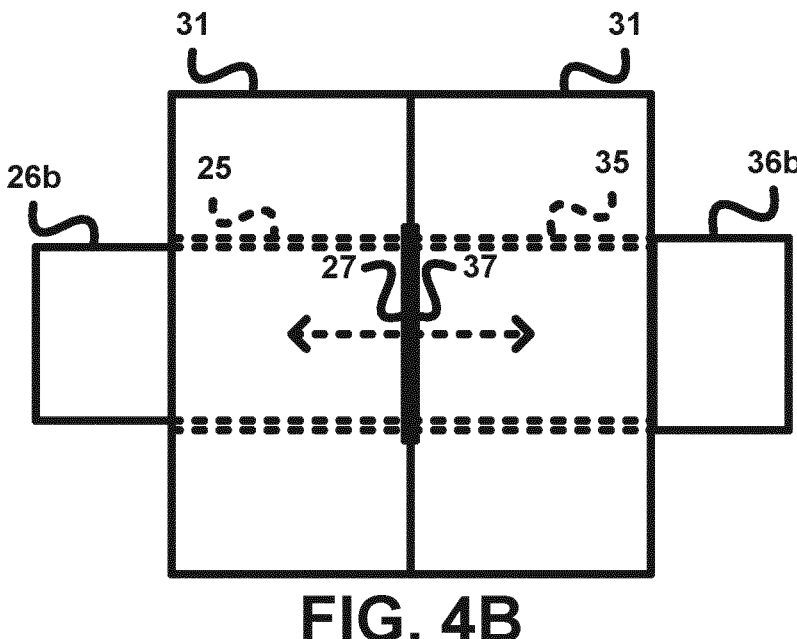

In one fluid exemplary embodiment of FIG. 3B, FIG. 4B illustrates a medical base 21 having a medical conduit segment 26b flush with medical conduit channel 25 and a patient base 31 having a patient conduit segment 36b flush with patient conduit channel 35 whereby a distal end of medical conduit segment 26b and a distal end of patient conduit segment 36b are in coaxial contact to establish the alignment of medical conduit channel 25 of medical base 21 and patient conduit channel 35 of patient base 31, whereby fluid may be communicated via channels 25 and 35 between tubes connected to a medical product and a patient. A seal 27 and a seal 37 are provided to prevent any fluid leakage from medical conduit segment 26b and patient conduit segment 36b.

For FIG. 4B, medical conduit segment 26b may represent a fluid tube from a medical fluid container (e.g., IV bag) or a friction fit or clamping coupler/adapter to a fluid tube of a medical fluid container.

For FIG. 4B, patient conduit segment 36b may represent a fluid tube from a patient or a friction fit or clamping coupler/adapter to a fluid tube of a patient.

An activation of magnetic connectivity interface (not shown for clarity) sustains the alignment of medical conduit channel 25 of medical base 21 and patient conduit channel 35 of patient base 31 whereby fluid may be communicated via channels 25 and 35 between tubes connected to a medical product and a patient.

Figure 5A:
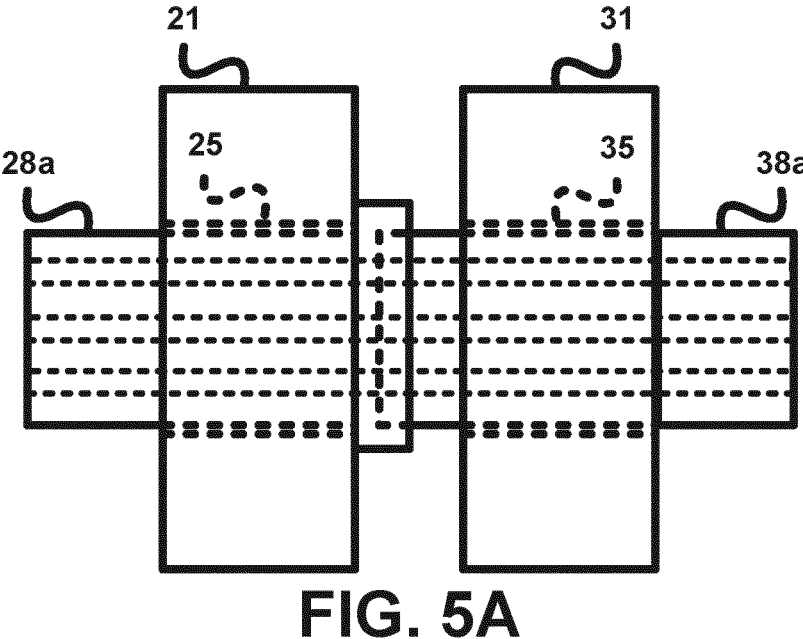

In one signal exemplary embodiment of FIG. 3A, FIG. 5A illustrates a medical base 21 having a medical conduit segment 28a extending through medical conduit channel 25 and a patient base 31 having a patient conduit segment 38a extending through patient conduit channel 35 whereby a distal end of medical conduit segment 28a receives a distal end of patient conduit segment 38a to establish the alignment of medical conduit channel 25 of medical base 21 and patient conduit channel 35 of patient base 31, whereby electric/optical signal(s) may be transferred via channels 25 and 35 between cables 1 connected to a medical equipment and a patient.

For FIG. 5A, medical conduit segment 28a may represent a cable to a piece of medical equipment, or a friction fit or clamping coupler/adapter to a cable of a piece of medical equipment.

For FIG. 5A, patient conduit segment 38a may represent a cable connected to a patient (e.g., ECG LEDs), or a friction fit or clamping coupler/adapter to a cable of connected to a patient.

An activation of magnetic connectivity interface (not shown for clarity) sustains the alignment of medical conduit channel 25 of medical base 21 and patient conduit channel 35 of patient base 31 whereby electric/optical signal(s), transferred via channels 25 and 35 between cables connected to a medical equipment and a patient.

Figure 5B:
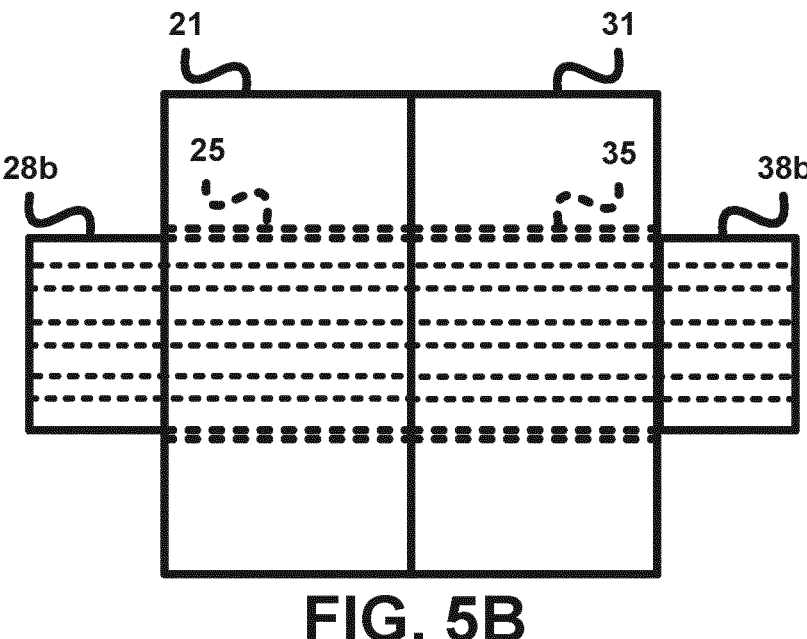

In one signal exemplary embodiment of FIG. 3B, FIG. 5B illustrates a medical base 21 having a medical conduit segment 28b extending through medical conduit channel 25 and a patient base 31 having a patient conduit segment 38b extending through patient conduit channel 35 whereby a distal end of medical conduit segment 28b receives a distal end of patient conduit segment 37a to establish the alignment of medical conduit channel 25 of medical base 21 and patient conduit channel 35 of patient base 31 whereby signal may be communicated via channels 25 and 35 between cables connected to a medical equipment and a patient. A seal 27 and a seal 37 are provided to prevent any electric/optical signal(s) leakage from medical conduit segment 28b and patient conduit segment 38b For FIG. 5B, medical conduit segment 28b may represent a cable to a piece of medical equipment, or a friction fit or clamping coupler/adapter to a cable of a piece of medical equipment.

For FIG. 5B, patient conduit segment 38b may represent a cable connected to a patient (e.g., ECG LEDs), or a friction fit or clamping coupler/adapter to a cable of connected to a patient.

An activation of magnetic connectivity interface (not shown for clarity) sustains the alignment of medical conduit channel 25 of medical base 21 and patient conduit channel 35 of patient base 31 whereby electric/optical signal(s) may be communicated via channels 25 and 35 between cables connected to a medical equipment and a patient.

Referring back to FIGS. 1A-1D, in practice, magnetic connectivity interface 22/32 may have any arrangement of metallic module(s) and ferromagnet(s) that provide for a secure connection of a desired magnetic strength between medical base 21 and patient base 31.

Figures 6A, 6B, 6C:
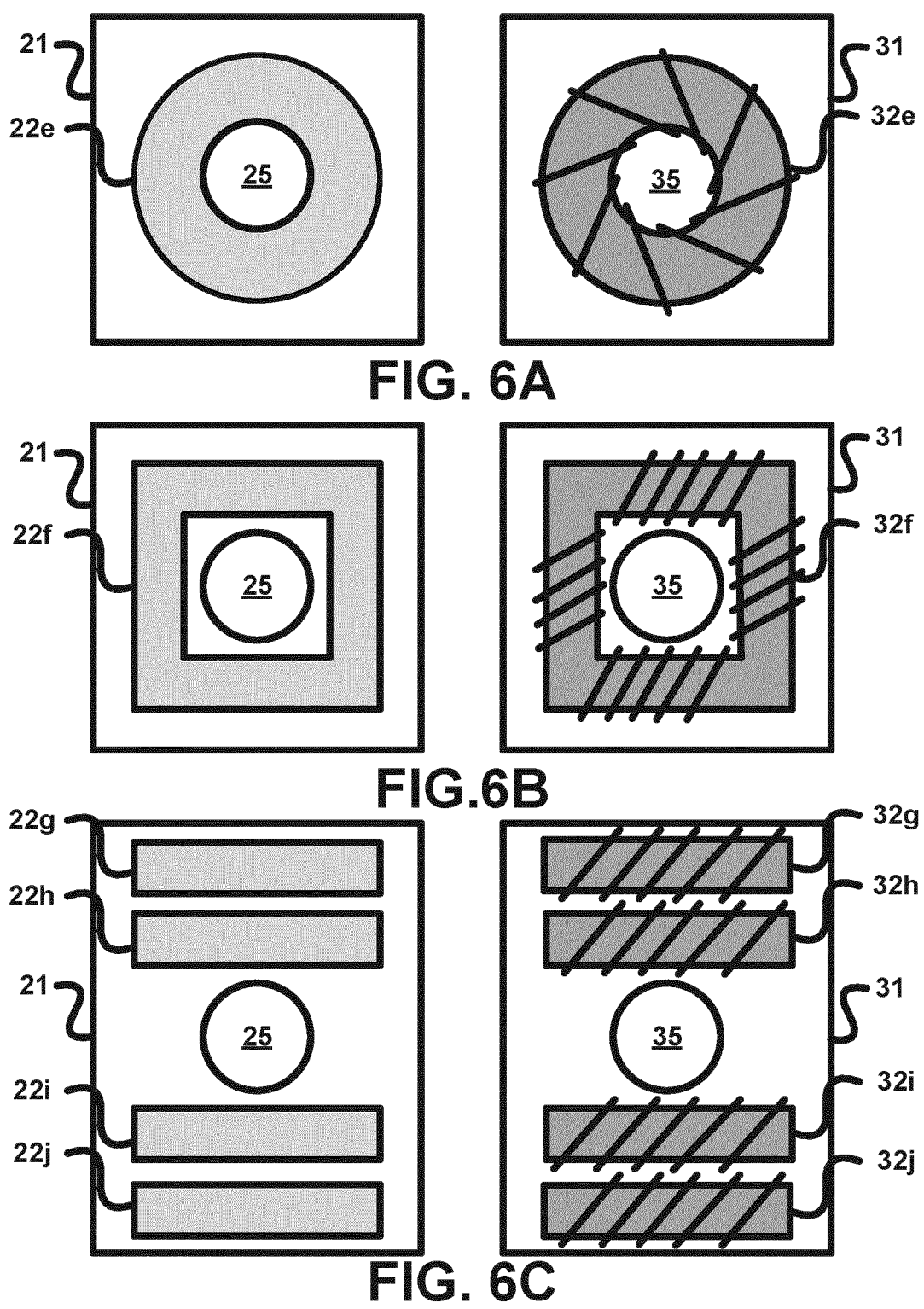
FIGS. 6A-6C illustrate exemplary embodiments of metallic modules and ferromagnets in accordance with the present disclosure.

In one exemplary embodiment magnetic connectivity interface 22/32 as shown in FIG. 6A, an annular metallic module 22e is exteriorly mounted (or alternatively integrated) to medical base 21 and an annular ferromagnet 32e, including ferromagnetic material encircled by a coil, is exteriorly mounted (or alternatively integrated) to patient base 31. Ferromagnet 32e may energized via a flow of current through the coil to create magnetic attraction of metallic module 22e to ferromagnet 32e. Conversely, ferromagnet 32e may deenergized absence a flow of current through the coil to impede any magnetic attraction of metallic module 22e to ferromagnet 32e.

In a second exemplary embodiment magnetic connectivity interface 22/32 as shown in FIG. 6B, a prismatic metallic module 22f is exteriorly mounted (or alternatively integrated) to medical base 21 and an prismatic ferromagnet 32*f,* including ferromagnetic material encircled by up to four (4) coils, is exteriorly mounted (or alternatively integrated) to patient base 31. Ferromagnet 32*f* may energized via a flow of current through the coil(s) to create magnetic attraction of metallic module 22*f* to ferromagnet 32*f*. Conversely, ferromagnet 32*f* may deenergized absence a flow of current through the coil(s) to impede any magnetic attraction of metallic module 22*f* to ferromagnet 32*f*.

In practice, if ferromagnet 32*f* employs two or more coils, then a flow of current through each coil may be individually controlled to vary the magnetic strength of the connection between medical base 21 and patient base 31.

In a third exemplary embodiment magnetic connectivity interface 22/32 as shown in FIG. 6C, metallic modules 22*g*-22*i* are exteriorly mounted (or alternatively integrated) to medical base 21 and ferromagnets 32*g*-32*i*, each including ferromagnetic material encircled by a coil, is exteriorly mounted (or alternatively integrated) to patient base 31. Each ferromagnet 32*g*-32*i* may be individually energized via a flow of current through an associated coil to create magnetic attraction of a corresponding one of metallic modules 22*g*-22*i* to that particular ferromagnet. Conversely, all ferromagnets 32*g*-32*i* may deenergized absence a flow of current through the coils to impede any magnetic attraction of metallic modules 22*g*-22*i* to ferromagnet 32*g*-32*i*.

In practice, a flow of current through each coil may be individually controlled to vary the magnetic strength of the connection between medical base 21 and patient base 31.

Referring back to FIGS. 1A-1D, in practice, medical strain sensor 70 and patient strain sensor 71 may incorporate one or more strain gauges adjoined to medical base 21 and patient base 31, respectively, and/or encircling medical conduit 23 and patient conduit 33, respectively.

Figure 7A:
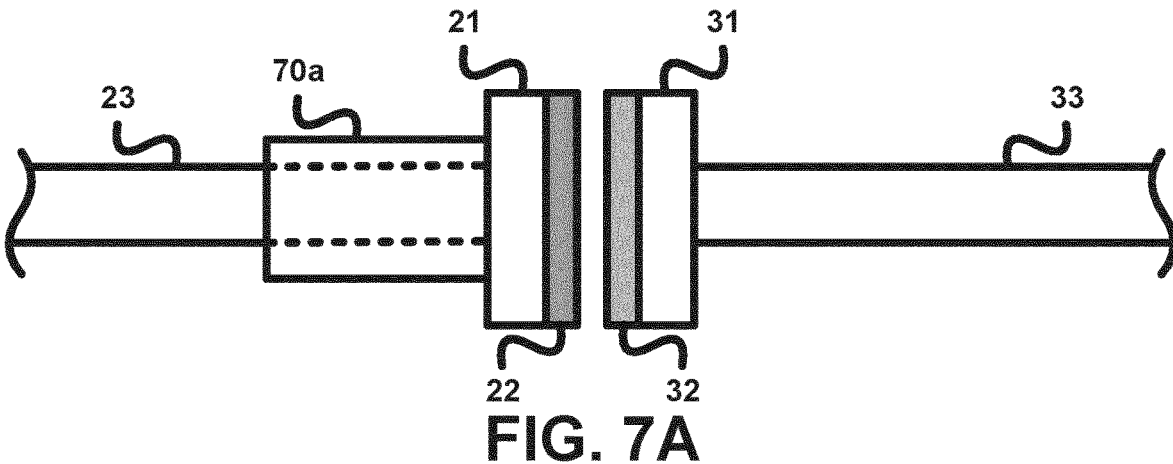
FIGS. 7A-7C illustrate exemplary embodiments of strain sensors in accordance with the present disclosure.

In one exemplary embodiment of medical strain sensor 70 as shown in FIG. 7A, an annular medical strain gauge 70*a* encircles medical conduit 23 and is adjoined to medical base 21 to sense a degree of strain applied by medical conduit 23 to medical base 21 and to sense a degree of strain applied by patient base 31 to medical base 21.

Figure 7B:
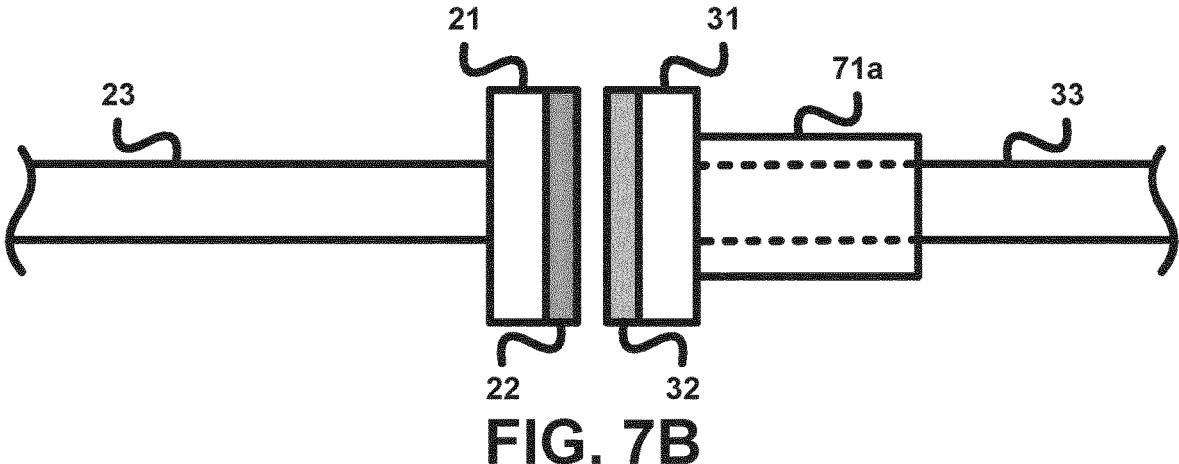

In one exemplary embodiment of patient strain sensor 71 as shown in FIG. 7B, an annular patient strain gauge 71*a* encircles patient conduit 33 and is adjoined to patient base 31 to sense a degree of strain applied by patient conduit 33 to patient base 31 and to sense a degree of strain applied by medical base 21 to patient base 31.

Figure 7C:
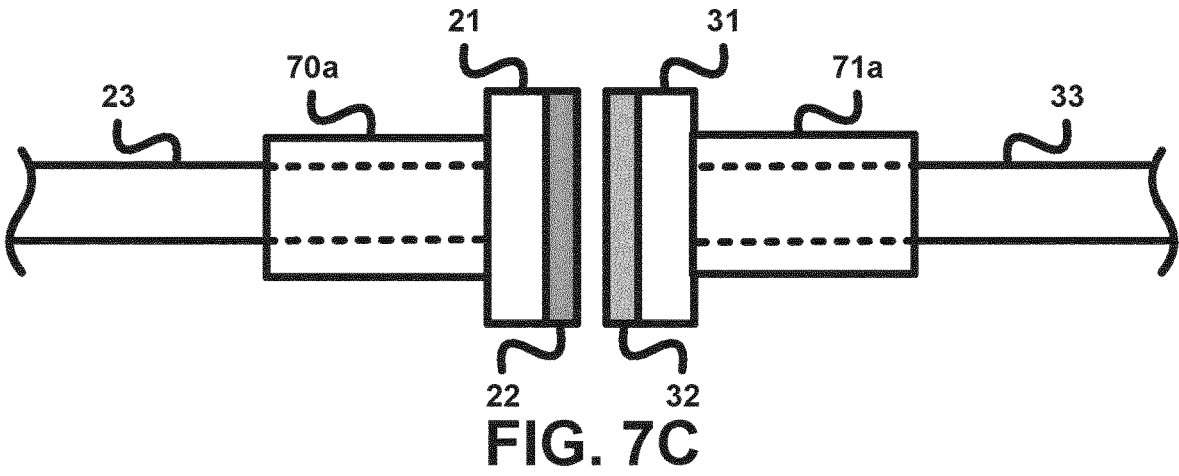

FIG. 7C shows an embodiment of medical strain sensor 70 and patient strain sensor 71 including the medical strain gauge 70*a* of FIG. 7A and patient strain gauge 71*a* of FIG. 7B.

Referring back to FIGS. 1A and 1D, in practice, ferromagnet controller 50 and power supply 60 are operated to control an energizing of magnetic connectivity interface 22 and 32 to activate and to control a de-energizing of magnetic connectivity interface 22 and 32 to deactivate the magnetic connectivity of magnetic connectivity interface 22 and 32. To this end, ferromagnet controller 50 and power supply 60 may collectively adjoined to medical base 21 or patient base 31, or may distributively adjoined between medical base 21 and patient base 31.

Figure 8A:
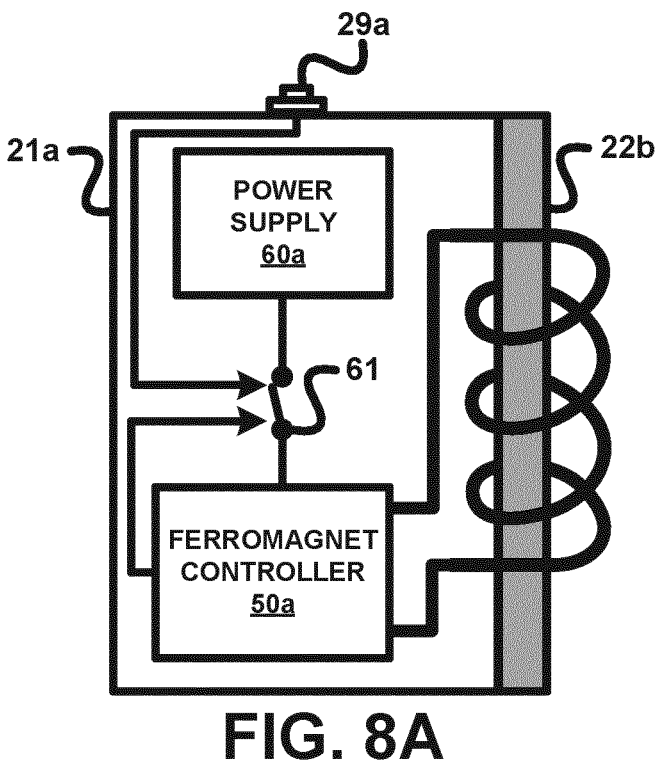

In one exemplary embodiment of ferromagnet controller 50 and power supply 60 as shown in FIG. 8A, a ferromagnet controller 50*a* and a power supply 60*a* are internally integrated within a medical base 21*a*. Power supply 60*a* is electrically connectable to ferromagnet controller 50*a* via a switch 61 (hardware and/or software implemented), and ferromagnet controller 50*a* is electrically connected to both ends of the coil of ferromagnet 22*b* (FIG. 2B). An opening and a closing of switch 61 is controlled by a manual activation/deactivation button 29*a* or ferromagnetic controller 50*a* to control an energizing and a de-energizing of ferromagnet 22*b* as will be further described in the present disclosure.

Figure 8B:
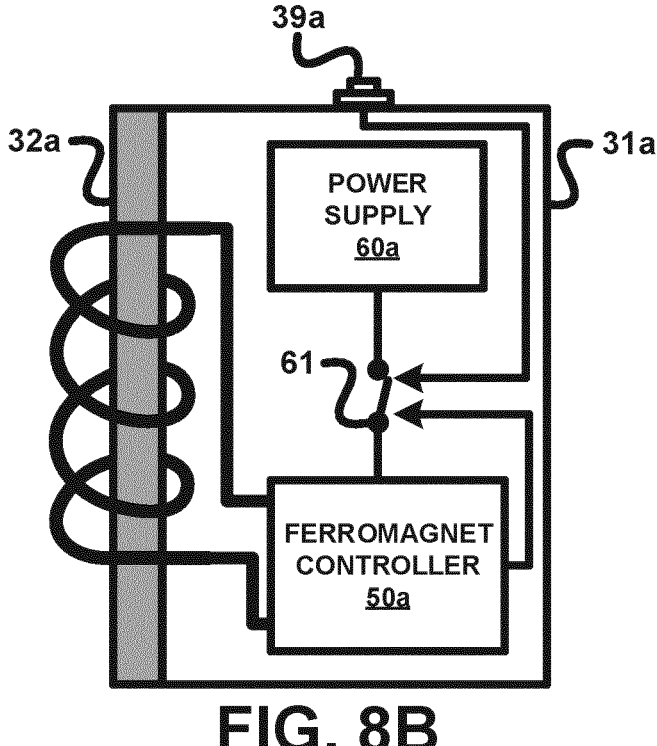

In a second exemplary embodiment of ferromagnet controller 50 and power supply 60 as shown in FIG. 8B, ferromagnet controller 50*a* and power supply 60*a* are internally integrated within a patient base 31*a*. Power supply 60*a* is electrically connectable to ferromagnet controller 50*a* via a switch 61, and ferromagnet controller 50*a* is electrically connected to both ends of the coil of ferromagnet 32*a* (FIG. 2A). An opening and a closing of switch 61 is controlled by a manual activation/deactivation button 39*a* or by ferromagnetic controller 50*a* to control an energizing and a de-energizing of ferromagnet 32*a* as will be further described in the present disclosure.

Figure 8C:
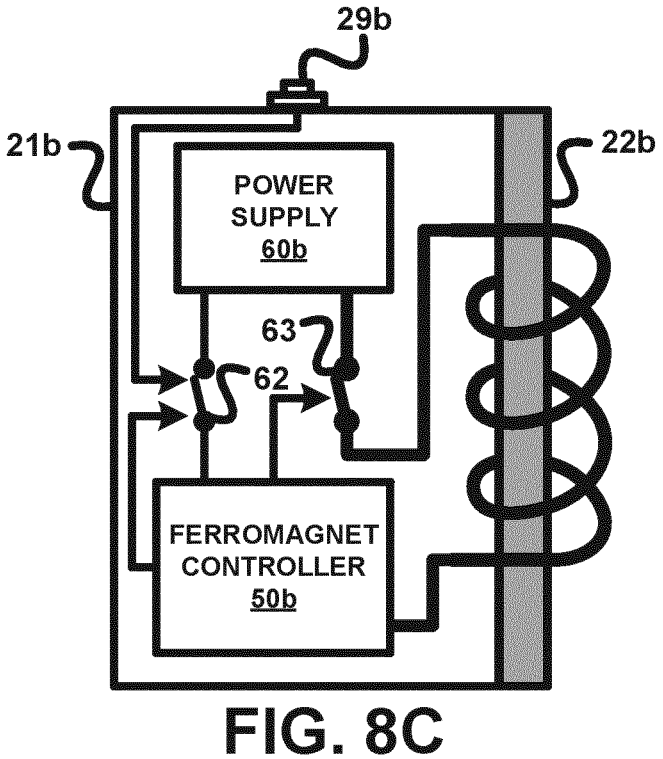

In a third exemplary embodiment of ferromagnet controller 50 and power supply 60 as shown in FIG. 8C, a ferromagnet controller 50*b* and a power supply 60*b* are internally integrated within a medical base 21*b*. Power supply 60*b* is electrically connectable to ferromagnet controller 50*b* via a switch 62 (hardware and/or software implemented) and electrically connectable to one end of the coil of ferromagnet 22*b* (FIG. 2B) via a switch 63 (hardware and/or software implemented). Ferromagnet controller 50*b* is electrically connected to the other end of the coil of ferromagnet 22*b*. To control an energizing and a de-energizing of ferromagnet 22*b*, an opening and a closing of switch 62 is controlled by a manual activation/deactivation button 29*b* or ferromagnet controller 50*b* and an opening and a closing of switch 63 is controlled by ferromagnet controller 50*b* as will be further described in the present disclosure.

Figure 8D:
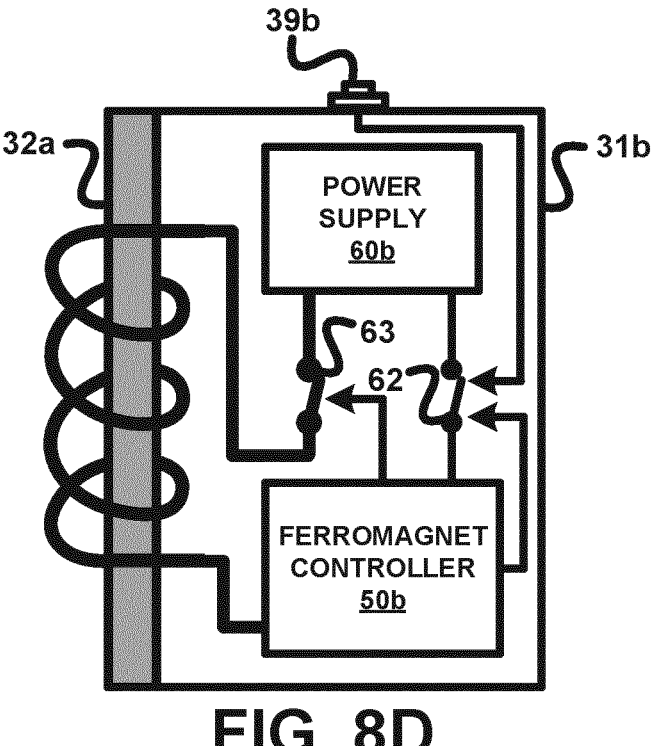

In a fourth exemplary embodiment of ferromagnet controller 50 and power supply 60 as shown in FIG. 8D, ferromagnet controller 50*b* and power supply 60*b* are internally integrated within a patient base 31*a*. Power supply 60*b* is electrically connectable to ferromagnet controller 50*b* via switch 62 and electrically connectable to one end of the coil of ferromagnet 32*a* (FIG. 2A) via switch 63. Ferromagnet controller 50*b* is electrically connected to the other end of the coil of ferromagnet 32*a*. To control an energizing and a de-energizing of ferromagnet 32*a*, an opening and a closing of switch 62 is controlled by a manual activation/deactivation button 39*b* or ferromagnet controller 50*b* and an opening and a closing of switch 63 is controlled by ferromagnet controller 50*b* as will be further described in the present disclosure.

Figures 9A, 9B:
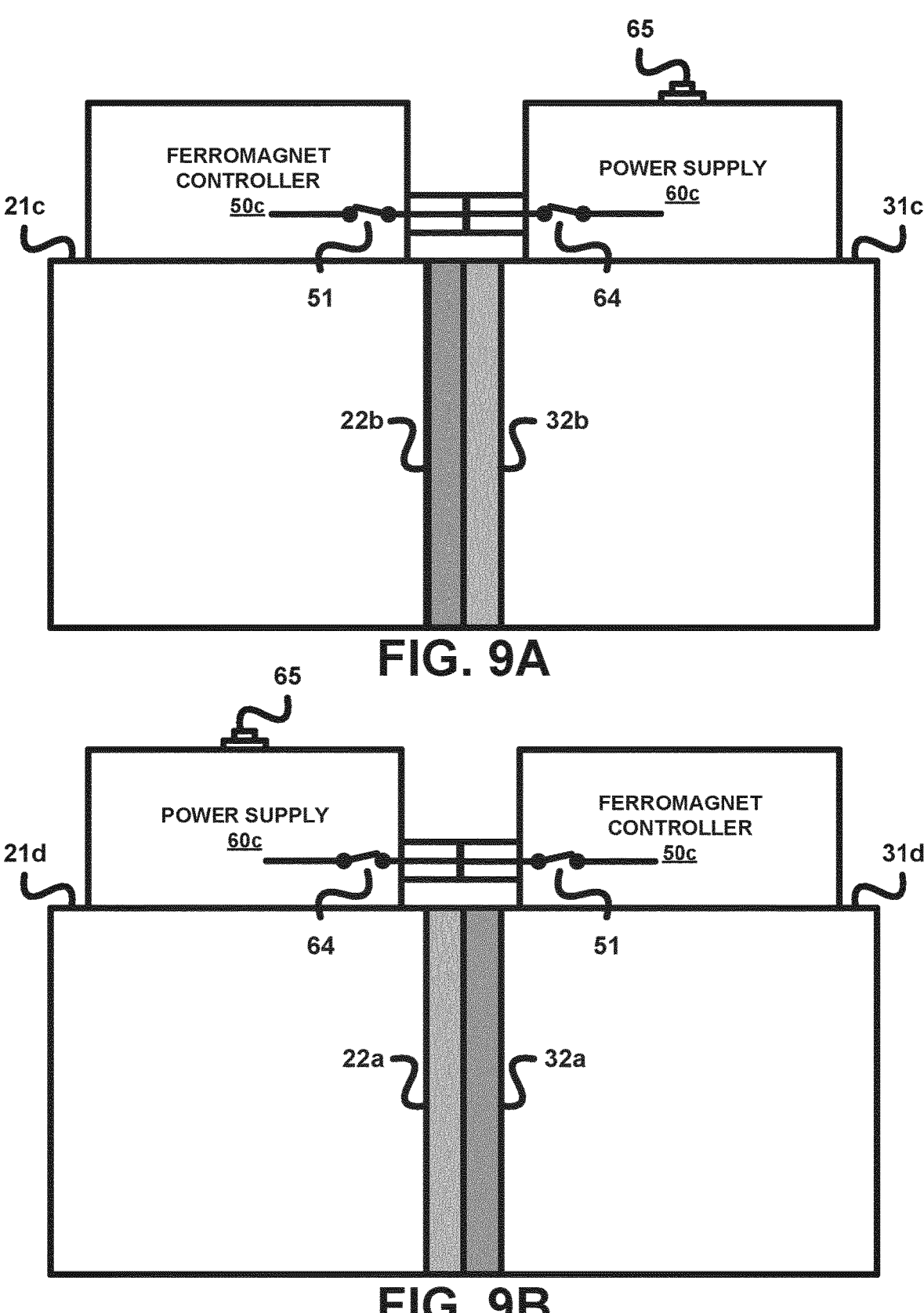

In a fifth exemplary embodiment of ferromagnet controller 50 and power supply 60 as shown in FIG. 9A, a ferromagnet controller 50*c* is exteriorly mounted to a medical base 21*c* and a power supply 60*c* is exteriorly mounted to a patient base 31*c* with ferromagnet controller 50*c* being electrically connected to power supply 60*c*. Ferromagnet controller 50*c* is further electrically connected to both ends of the coil (not shown) of ferromagnet 22*b* (FIG. 2B). Ferromagnetic controller 50*c* include a switch 51 (hardware and/or software implemented) and power supply 60*c* includes a switch 64 (hardware and/or software implemented) and a manual activation/deactivation button 65 to control an energizing and a de-energizing of ferromagnet 22*b* as will be further described in the present disclosure.

In a sixth exemplary embodiment of ferromagnet controller 50 and power supply 60 as shown in FIG. 9B, ferromagnet controller 50*c* is exteriorly mounted to a patient base 31*c* and power supply 60c is exteriorly mounted to medical base 21c with ferromagnet controller 50c being electrically connected to power supply 60c. Ferromagnet controller 50c is further electrically connected to both ends of the coil (not shown) of ferromagnet 32a (FIG. 2A). Ferromagnetic controller 50c include switch 51 (hardware and/or software implemented) and power supply 60c includes switch 64 (hardware and/or software implemented) and manual activation/deactivation button 65 to control an energizing and a de-energizing of ferromagnet 32a as will be further described in the present disclosure.

Referring back to FIGS. 1A and 1D, in practice, power supply 60 may be any type of power supply as known in the art of the present disclosure and hereinafter conceived, and ferromagnet controller 50 incorporates circuitry, hardware, firmware and/or software to implement a smart medical connecting method of the present disclosure as will be further described in the present disclosure.

Figures 10A, 10B:
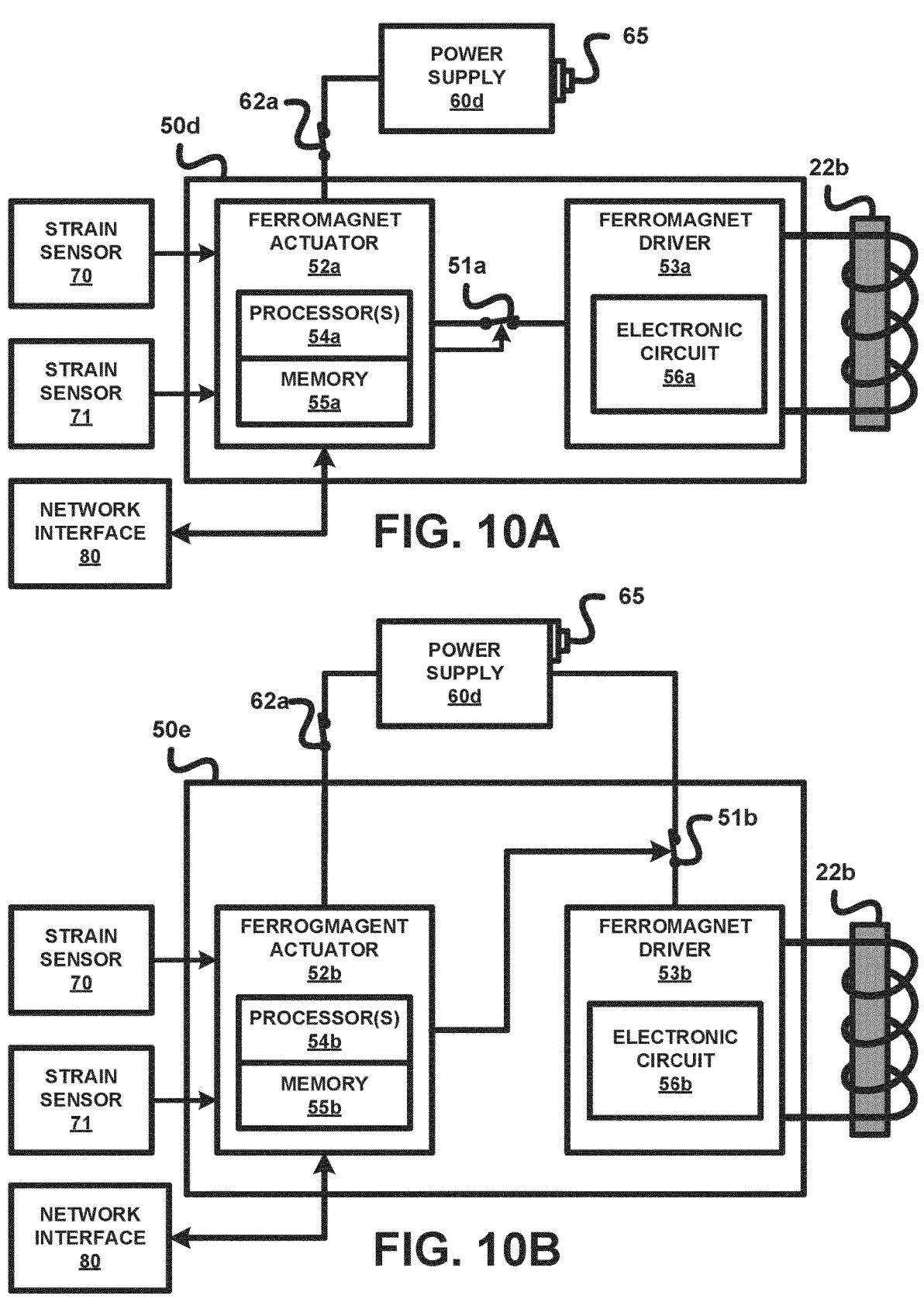
FIGS. 10A and 10B illustrate exemplary embodiments of a ferromagnet controller in accordance with the present disclosure.

In one exemplary embodiment as shown in FIG. 10A, a ferromagnet controller 50d includes a ferromagnet actuator 52a electrically connectable to a ferromagnet driver 53a via a switch 51a (hardware and/or software implemented), and a power supply 60d is electrically connectable to ferromagnet actuator 52a via a switch 62a (hardware and/or software implemented). Additionally, medical strain sensor 70 and/or patient strain sensor 71 are in electrical communication (wired or wireless) with ferromagnet actuator 52a, and an optional network interface 80 may also be in electrical communication (wired or wireless) with ferromagnetic actuator 52a.

Ferromagnet actuator 52a employs one or more processors 54a and non-transitory memory 55a to implement a smart medical connecting method of the present disclosure for controlling an opening and closing of switch 51a and/or switch 62a based on signals/information from medical strain sensor 70, patient strain sensor 71 and/or network interface 80 as will be further described in the present disclosure.

In practice, processor(s) 54a may be any hardware device, as known in the art of the present disclosure or hereinafter conceived, capable of executing instructions stored in non-transitory memory 55a or otherwise processing data. In a non-limiting example, the processor(s) 54a may include a microprocessor, field programmable gate array (FPGA), application-specific integrated circuit (ASIC), or other similar devices.

The non-transitory memory 55a may include various memories, as known in the art of the present disclosure or hereinafter conceived, including, but not limited to, L1, L2, or L3 cache or system memory. In a non-limiting example, the non-transitory memory 55a may include static random access memory (SRAM), dynamic RAM (DRAM), flash memory, read only memory (ROM), or other similar memory devices.

Ferromagnet driver 53a employs electronic circuit 56a, or alternatively processor(s) and non-transitory memory for controlling a flow of current through a ferromagnet (e.g., ferromagnet 22b as shown) when both switches 51a and 62a are closed.

In a second exemplary embodiment as shown in FIG. 10B, a ferromagnet controller 50e includes a ferromagnet actuator 52b for actuating ferromagnet driver 53b via a switch 51b (hardware and/or software implemented), and power supply 60d is electrically connectable to ferromagnet actuator 52a via a switch 62a (hardware and/or software implemented) and electrically connected to ferromagnet driver 53b via switch 51b. Additionally, medical strain sensor 70 and/or patient strain sensor 71 are in electrical communication (wired or wireless) with ferromagnet actuator 52b, and an optional network interface 80 may also be in electrical communication (wired or wireless) with ferromagnetic actuator 52b.

Ferromagnet actuator 52b employs one or more processors 54b and non-transitory memory 55b to implement a smart medical connecting method of the present disclosure for controlling an opening and closing of switch 51b and/or switch 62a based on signals/information from medical strain sensor 70, patient strain sensor 71 and/or network interface 80 as will be further described in the present disclosure.

In practice, processor(s) 54b may be any hardware device, as known in the art of the present disclosure or hereinafter conceived, capable of executing instructions stored in non-transitory memory 55b or otherwise processing data. In a non-limiting example, the processor(s) 54b may include a microprocessor, field programmable gate array (FPGA), application-specific integrated circuit (ASIC), or other similar devices.

The non-transitory memory 55b may include various memories, as known in the art of the present disclosure or hereinafter conceived, including, but not limited to, L1, L2, or L3 cache or system memory. In a non-limiting example, the non-transitory memory 55b may include static random access memory (SRAM), dynamic RAM (DRAM), flash memory, read only memory (ROM), or other similar memory devices.

Ferromagnet driver 53b employs electronic circuit 56b, or alternatively processor(s) and non-transitory memory for controlling a flow of current through a ferromagnet (e.g., ferromagnet 22b as shown) when both switches 51b and 62a are closed.

Figures 11A, 11B:
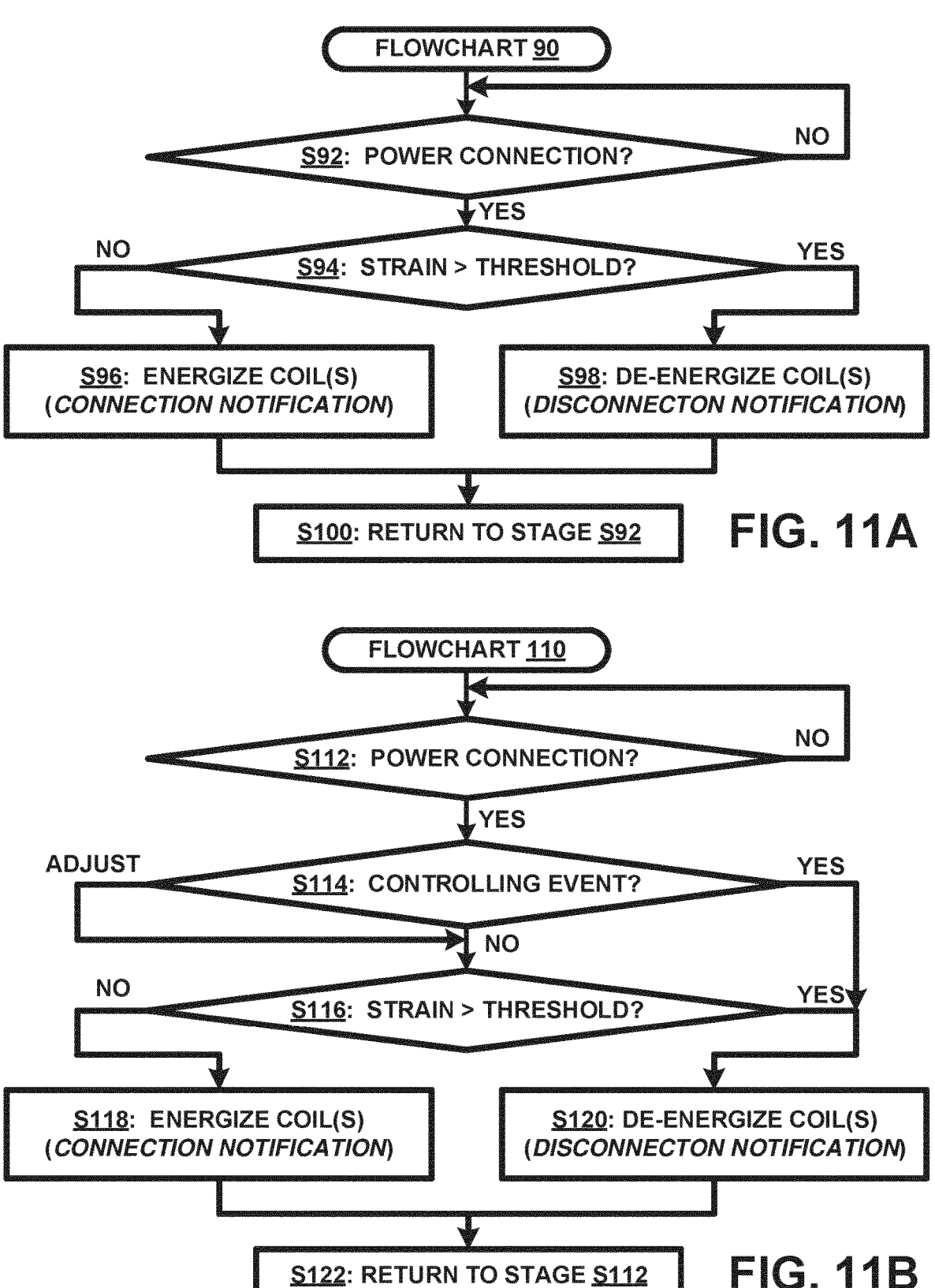
FIGS. 11A and 11B illustrate exemplary flowcharts representative of embodiments of smart medical connection methods in accordance with the present disclosure.

To further facilitate an understanding of the present disclosure, the following description of FIGS. 11A and 11B teach exemplary embodiments of smart medical methods in accordance with the present disclosure. From the description of FIGS. 11A and 11B, those having ordinary skill in the art of the present disclosure will appreciate how to apply the present disclosure to formulate and use additional embodiments of smart medical methods in accordance with the present disclosure.

FIG. 11A shows a flowchart 90 representative of one exemplary embodiment of a smart medical connecting method of the present disclosure. Flowchart 90 will be described in the context of ferromagnet controller 50 and power supply 60 of FIGS. 1A-1D. Nonetheless, those having ordinary skill in the art will appreciate the applicability of the flowchart 90 to the exemplary embodiments of ferromagnet controller 50 and power supply 60 of FIGS. 8A-10B and additional embodiments of ferromagnet controller 50 and power supply 60 in accordance with the present disclosure.

Referring to FIG. 11A, a stage S92 of flowchart 90 encompasses a push button of power supply 60 being activated to power connect power supply 60 to ferromagnet controller 50 or deactivated to power disconnect power supply 60 from ferromagnet controller 50.

If push button of power supply 60 is activated to power connect power supply 60 to ferromagnet controller 50, then a stage S94 of flowchart 90 encompasses ferromagnet controller 50 ascertaining if:

(1) medical strain sensor 70 (if employed) and/or patient strain sensor 71 (if employed) is(are) sensing a level of strain being applied to the medical base 21 and/or the patient base 31 designated as unharmful to the patient and/or the medical product (i.e., a connection strain being less than a magnetic connectivity threshold); or (2) medical strain sensor 70 (if employed) and/or patient strain sensor 71 (if employed) is(are) sensing a level of strain being applied to the medical base 21 and/or the patient base 31 designated as potentially harmful to the patient and/or the medical product (i.e., a disconnection strain exceeding the magnetic connectivity threshold).

If ferromagnet controller 50 ascertains a connection strain during stage S94, then ferromagnet controller 50 proceeds to a stage S96 of flowchart 90 to control an energizing of the ferromagnet(s) of magnetic connectivity interface 22/32 and then returns to stage S92.

In practice of stage S96, ferromagnet controller 50 may be configured to fully energize the ferromagnet(s) of magnetic connectivity interface 22/32 (i.e., a degree of current flow through the ferromagnet(s) is set to establish a designated level of magnetic connectivity of interface 22/32), whereby ferromagnet controller 50 may be provide a connection notification via network interface 80 to connected network systems and/or workstations.

Alternatively in practice of stage S96, ferromagnet controller 50 may be configured to adapt the energizing the ferromagnet(s) of magnetic connectivity interface 22/32 to the strain level being applied to medical base 21 and patient base 31 (i.e., a degree of current flow through the ferromagnet(s) is to establish a minimum level of magnetic connectivity of interface 22/32 to counteract the strain level), whereby ferromagnet controller 50 may also provide a warning connection notification via network interface 80 to connected network systems and/or workstation as the strain level is approaching the threshold.

If ferromagnet controller 50 ascertains a disconnection strain during stage S94, then ferromagnet controller 50 proceeds to a stage S98 of flowchart 90 to control a de-energizing of the ferromagnet(s) of magnetic connectivity interface 22/32 and then returns to stage S92.

In practice of stage S98, ferromagnet controller 50 may be configured to fully de-energize the ferromagnet(s) of magnetic connectivity interface 22/32 (i.e., zero current flow through the ferromagnet(s) to deactivate the magnetic connectivity of interface 22/32), whereby ferromagnet controller 50 may be provide a disconnection notification via network interface 80 to connected network systems and/or workstations.

Alternatively in practice of stage S98, ferromagnet controller 50 may be configured to adapt the de-energizing the ferromagnet(s) of magnetic connectivity interface 22/32 to the strain level being applied to medical base 21 and patient base 31 (i.e., a degree of current flow through the ferromagnet(s) is to establish a minimum level of magnetic connectivity of interface 22/32 to counteract the strain level), whereby ferromagnet controller 50 may also provide a warning disconnection notification via network interface 80 to connected network systems and/or workstations as the strain level is substantially exceeding the threshold.

In practice of flowchart 90, the threshold may be set during the manufacture of a smart medical controller of the present disclosure or may be adjusted by clinical staff in the field.

Also in practice of flowchart 90, the strain level of stage S94 may equate an instantaneous strain level to provide an immediate response to a disconnection strain, or alternatively, the strain level of stage S94 may be an average/trending strain level to negate immediate response to a disconnection strain (e.g., a patient is rolling in bed).

FIG. 11B shows a flowchart 110 representative of a second exemplary embodiment of a smart medical connecting method of the present disclosure. Flowchart 110 will also be described in the context of ferromagnet controller 50 and power supply 60 of FIGS. 1A-1D. Nonetheless, those having ordinary skill in the art will appreciate the applicability of the flowchart 110 to the exemplary embodiments of ferromagnet controller 50 and power supply 60 of FIGS. 8A-10B and additional embodiments of ferromagnet controller 50 and power supply 60 in accordance with the present disclosure.

Referring to FIG. 11B, a stage S112 of flowchart 110 encompasses a push button of power supply 60 being activated to power connect power supply 60 to ferromagnet controller 50 or deactivated to power disconnect power supply 60 from ferromagnet controller 50.

If push button of power supply 60 is activated to power connect power supply 60 to ferromagnet controller 50, the a stage S114 of flowchart 100 encompasses ferromagnet controller 50 ascertaining if an overriding event has been communicated to ferromagnet controller 50 via network interface 80 from a clinical staff, the medical product or a physiological sensor. In practice, an overriding event is any circumstances associated with the patient and/or the medical product, other than strain on the smart medical connector, that is either deemed potentially harmful to the patient and/or the medical product necessitates a disconnection of the smart medical connector or deemed unharmful patient and the medical product yet requiring an adjustment to the threshold or magnetic connectivity level of the connection between a patients and the medical product.

For example, unnecessary medical equipment may automatically be disconnected in emergency situation when a cardiac arrest of the patient is detected by a monitoring device or a clinical staffer.

Also by example, EHR information or monitoring device information may be used for adjusting the threshold or magnetic connectivity level of the connection between a patient and the medical product.

If ferromagnet controller 50 ascertains an overriding event has been communicated to ferromagnet controller 50 during stage S114, then ferromagnet controller 50 will either proceed to a stage S116 of flowchart 110 if the overriding event requires an adjustment to the threshold or magnetic connectivity of the connection between the patient and the medical product, or proceed to a stage S120 of flowchart 110 if overriding event requires necessitates a disconnection of the smart medical connector, Otherwise, if ferromagnet controller 50 ascertains an overriding event has not been communicated to ferromagnet controller 50 during stage S114, the ferromagnetic controller proceeds to stage S116 of flowchart 110 without any adjustment to the threshold or magnetic connectivity of the connection between the patient and the medical product.

Stage S116 encompasses ferromagnet controller 50 ascertaining if:

(1) medical strain sensor 70 (if employed) and/or patient strain sensor 71 (if employed) is(are) sensing a level of strain being applied to the medical base 21 and/or the patient base 31 designated as unharmful to the patient and/or the medical product (i.e., a connection strain being less than a magnetic connectivity threshold); or (2) medical strain sensor 70 (if employed) and/or patient strain sensor 71 (if employed) is(are) sensing a level of strain being applied to the medical base 21 and/or the patient base 31 designated as potentially harmful to the patient and/or the medical product (i.e., a disconnection strain exceeding the magnetic connectivity threshold).

If ferromagnet controller 50 ascertains a connection strain during stage S116, then ferromagnet controller 50 proceeds to a stage S118 of flowchart 110 to control an energizing of the ferromagnet(s) of magnetic connectivity interface 22/32 and then returns to stage S112.

In practice of stage S118, ferromagnet controller 50 may be configured to fully energize the ferromagnet(s) of magnetic connectivity interface 22/32 (i.e., a degree of current flow through the ferromagnet(s) is set to establish a designated level of magnetic connectivity of interface 22/32), whereby ferromagnet controller 50 may be provide a connection notification via network interface 80 to connected network systems and/or workstations.

Alternatively in practice of stage S118, ferromagnet controller 50 may be configured to adapt the energizing the ferromagnet(s) of magnetic connectivity interface 22/32 to the strain level being applied to medical base 21 and patient base 31 (i.e., a degree of current flow through the ferromagnet(s) is to establish a minimum level of magnetic connectivity of interface 22/32 to counteract the strain level), whereby ferromagnet controller 50 may also provide a warning connection notification via network interface 80 to connected network systems and/or workstation as the strain level is approaching the threshold.

If ferromagnet controller 50 ascertains a disconnection strain during stage S116, then ferromagnet controller 50 proceeds to a stage S120 of flowchart 110 to control a de-energizing of the ferromagnet(s) of magnetic connectivity interface 22/32 and then returns to stage S112.

In practice of stage S120, ferromagnet controller 50 may be configured to fully de-energize the ferromagnet(s) of magnetic connectivity interface 22/32 (i.e., zero current flow through the ferromagnet(s) to deactivate the magnetic connectivity of interface 22/32), whereby ferromagnet controller 50 may be provide a disconnection notification via network interface 80 to connected network systems and/or workstations.

Alternatively in practice of stage S120, ferromagnet controller 50 may be configured to adapt the de-energizing the ferromagnet(s) of magnetic connectivity interface 22/32 to the strain level being applied to medical base 21 and patient base 31 (i.e., a degree of current flow through the ferromagnet(s) is to establish a minimum level of magnetic connectivity of interface 22/32 to counteract the strain level), whereby ferromagnet controller 50 may also provide a warning disconnection notification via network interface 80 to connected network systems and/or workstations as the strain level is substantially exceeding the threshold.

In practice of flowchart 110, the threshold may be set during the manufacture of a smart medical controller of the present disclosure or may be adjusted by clinical staff in the field.

Also in practice of flowchart 110, the strain level of stage S116 may equate an instantaneous strain level to provide an immediate response to a disconnection strain, or alternatively a the strain level of stage S116 may be an average/trending strain level to negate immediate response to a disconnection strain.

Figures 12A, 12B:
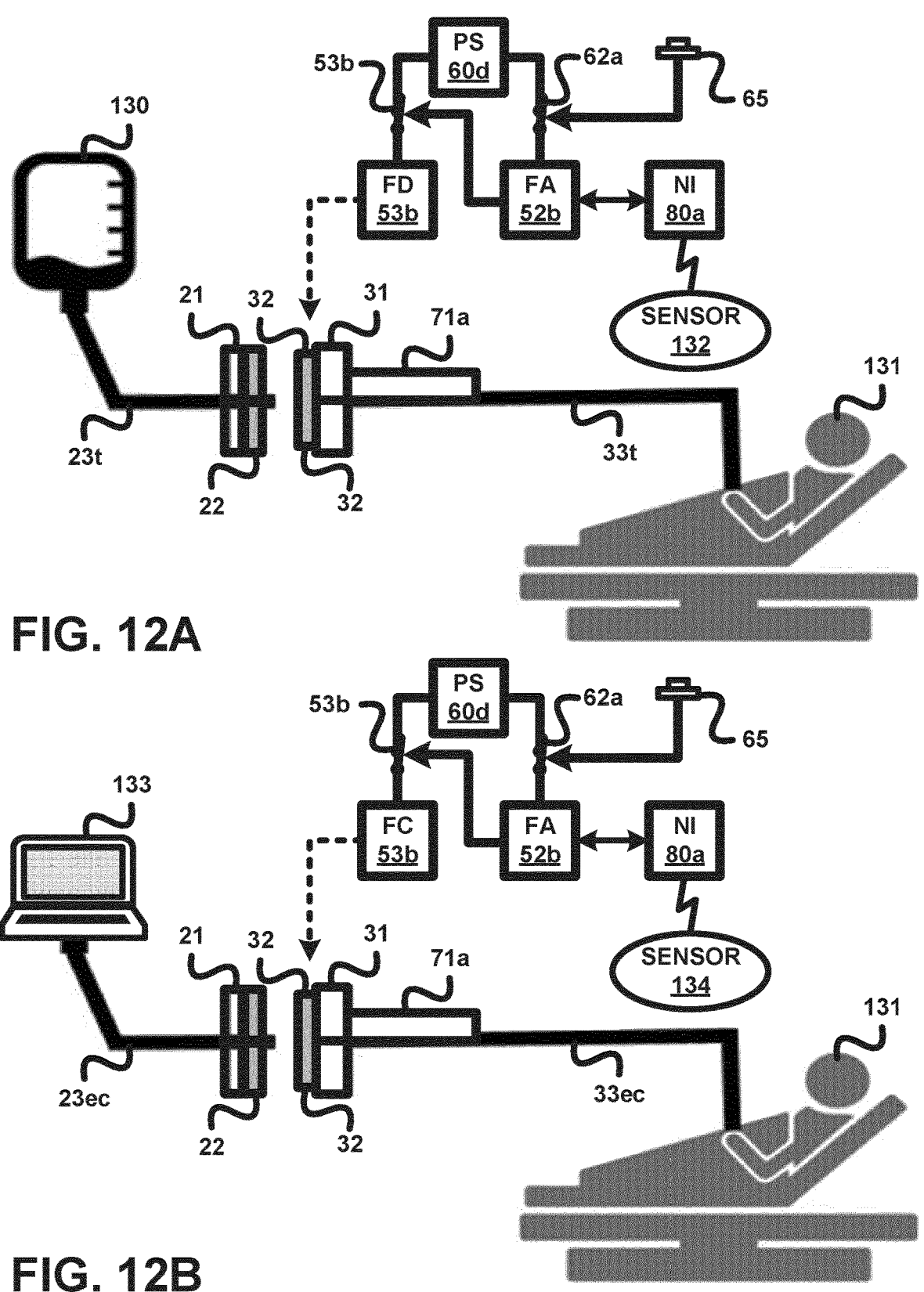
FIGS. 12A and 12B illustrate exemplary smart medical connections in accordance with the present disclosure.

To further facilitate an understanding of the present disclosure, the following description of FIGS. 12A and 12B illustrates exemplary smart medical connections in accordance with the present disclosure. From the description of FIGS. 12A and 12B, those having ordinary skill in the art of the present disclosure will appreciate additional smart medical connections in accordance with the present disclosure.

Referring to FIG. 12A, a smart medical connector of the present disclosure is being set up to feed an IV bag 130 to a patient 131 via tubes 23t and 33t. More particularly, medical base 21 and patient base 31 are aligned whereby if powered on via button 65, then magnetic connectivity interface 22/32 will be energized via ferromagnet actuator 52b, ferromagnet driver 53b and power supply 60d to establish and maintain a fluid communication of tubes 23t and 33t via the conduit channels of medical base 21 and patient base 31 until such time (1) the smart medical connector is powered off via button 65, (2) patient strain sensor 71a is sensing a disconnection strain being applied to medical base 21 and patient base 31 and/or (3) sensor 132 or a clinical staffer senses an emergency situation with patient 131.

In practice, magnetic connectivity interface 22/32 may include magnetic activated shutters to uncover the conduit channels of medical base 21 and patient base 31 when magnetic connectivity interface 22/32 is partially or fully energized and to cover the conduit channels of medical base 21 and patient base 31 when magnetic connectivity interface 22/32 is significantly or fully de-energized.

Referring to FIG. 12B, a smart medical connector of the present disclosure is being set up to connect an ECG monitor to a patient 131 via electric cables 23ec and 33ec. More particularly, medical base 21 and patient base 31 are aligned whereby if powered on via button 65, then magnetic connectivity interface 22/32 will be energized via ferromagnet actuator 52b, ferromagnet driver 53b and power supply 60d to establish and maintain an electric signal communication between electrical cables 23ec and 33ec via the conduit channels of medical base 21 and patient base 31 until such time (1) the smart medical connector is powered off via button 65, (2) patient strain sensor 71a is sensing a disconnection strain being applied to medical base 21 and patient base 31 and/or (3) sensor 132 or a clinical staffer senses an emergency situation with patient 131.

In practice, magnetic connectivity interface 22/32 may include magnetic activated levers to separate the conduit channels of medical base 21 and patient base 31 when magnetic connectivity interface 22/32 is significantly or fully de-energized.

Referring to FIGS. 1A-12B, those having ordinary skill in the art of the present disclosure will appreciate numerous benefits of the present disclosure including, but not limited to smart medical connections of the present disclosure involving a sensing of a potentially harmful strain on a connection between a patient and a medical product, and further involves an automatic disconnecting of the patient from the medical product due to the sensed potentially harmful strain to thereby impede, hopefully prevent, any harm to patient.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A smart medical connector, comprising:
a medical base having a medical conduit channel;
a patient base having a patient conduit channel;
a magnetic connectivity interface including at least one metallic module and at least one ferromagnet distributively adjoined to the medical base and the patient base, and
a magnetic connectivity manager including a power supply, a ferromagnet controller and at least one strain sensor collectively adjoined to one of the medical base or the patient base, or distributively adjoined to the medical base and the patient base,
wherein the magnetic connectivity manager is configured to controllably energize the at least one ferromagnet in response to a sensing by the at least one strain sensor of a connection strain on at least one of the medical base and the patient base, and
wherein the magnetic connectivity manager is configured to controllably deenergize the at least one ferromagnet in response a sensing by the at least one strain sensor of a disconnection strain on at least one of the medical base and the patient base,
wherein, in response to the energizing of the at least one ferromagnet, the magnetic connectivity interface is configured to activate a magnetic connectivity between the at least one metallic module and the at least one ferromagnet for interfacing the medical conduit channel and the patient conduit channel, and
wherein, in response to the deenergizing of the at least one ferromagnet, the magnetic connectivity interface is configured to deactivate the magnetic connectivity between the at least one metallic module and the at least one ferromagnet for interfacing the medical conduit channel and the patient conduit channel.

2. The smart medical connector of claim 1, wherein the medical base includes a medical conduit in at least one of a fluid communication and an electrical communication with the medical conduit channel.

3. The smart medical connector of claim 1, wherein the medical conduit channel is configured to establish at least one of a fluid communication and an electrical communication with a medical conduit.

4. The smart medical connector of claim 1, wherein the patient base includes a patient conduit in at least one of a fluid communication and an electrical communication with the patient conduit channel.

5. The smart medical connector of claim 1, wherein the patient conduit channel is configured to establish at least one of a fluid communication and an electrical communication with a patient conduit.

6. The smart medical connector of claim 1,
wherein the at least one metallic module is adjoined to the medical base; and
wherein the at least one ferromagnet is adjoined to the patient base.

7. The smart medical connector of claim 6, wherein the magnetic connectivity interface further includes at least one of:
an additional at least one metallic module adjoined to the patient base; or
an additional at least one ferromagnet adjoined to the medical base.

8. The smart medical connector of claim 1,
wherein the at least one metallic module is adjoined to the patient base; and
wherein the at least one ferromagnet is adjoined to the medical base.

9. The smart medical connector of claim 8, wherein the magnetic connectivity interface further includes at least one of:
an additional at least one metallic module adjoined to the medical base; or
an additional at least one ferromagnet adjoined to the patient base.

10. The smart medical connector of claim 1,
wherein the power supply is adjoined to the medical base; and
wherein the ferromagnet controller is adjoined to the patient base.

11. The smart medical connector of claim 1,
wherein the power supply is adjoined to the patient base; and
wherein the ferromagnet controller is adjoined to the medical base.

12. The smart medical connector of claim 1, further comprising a ferromagnetic driver, wherein the ferromagnetic driver is switchably connected to the power supply; wherein the ferromagnetic driver is connected to the at least one ferromagnet; and wherein the ferromagnet controller is configured to controllably connect the power supply to the at least one ferromagnet to energize the at least one ferromagnet.

13. The smart medical connector of claim 12, wherein at least one of:

the power supply is configured to controllably connect the power supply to the ferromagnetic driver to power on the ferromagnetic driver; or the ferromagnetic driver is configured to controllably connect the power supply to the ferromagnetic driver to power off the ferromagnetic driver.

14. The smart medical connector of claim 1, wherein the power supply is switchably connected to the at least one ferromagnet; and wherein the ferromagnet controller is configured to controllably connect the power supply to the ferromagnet to energize the at least one ferromagnet.

15. The smart medical connector of claim 14, wherein ferromagnetic driver is switchably connected to the power supply; and wherein at least one of:

the power supply is configured to controllably connect the power supply to the ferromagnetic driver to power on the ferromagnetic driver; or the ferromagnetic driver is configured to controllably connect the power supply to the ferromagnetic driver to power off the ferromagnetic driver.

16. A smart medical connecting method for a smart medical connector including a medical base having a medical conduit channel, a patient base having a patient conduit channel, and a magnetic connectivity interface including at least one metallic module and at least one ferromagnet distributively adjoined to the medical base and the patient base, the smart medical connecting method comprising:

energizing the at least one ferromagnet in response to a powering on of the smart medical connector and further in response to a sensing of a connection strain on at least one of the medical base and the patient base, wherein, in response to the energizing of the at least one ferromagnet, the magnetic connectivity interface activates a magnetic connectivity between the at least one metallic module and the at least one ferromagnet for interfacing the medical conduit channel and the patient conduit channel, and deenergizing the at least one ferromagnet in response to at least one of a powering down of the smart medical connector and a sensing of a disconnection strain on the at least one of the medical base and the patient base, wherein, in response to the deenergizing of the at least one ferromagnet, the magnetic connectivity interface deactivates the magnetic connectivity between the at least one metallic module and the at least one ferromagnet for interfacing the medical conduit channel and the patient conduit channel.

17. The smart medical connecting method of claim 16, further comprising:

transmitting a notification of a deactivation of the magnetic connectivity between the medical base and the patient base including the magnetic connectivity interface between the medical conduit channel and the patient conduit channel.

18. The smart medical connecting method of claim 16, further comprising:

adjusting a threshold between the connection strain and the disconnection strain.

19. The smart medical connecting method of claim 16, further comprising:

deenergizing the at least one ferromagnet in response to an overriding event.

20. The smart medical connecting method of claim 16, further comprising:

adjusting an energizing level of the at least one ferromagnet to adjust a strength of the magnetic connectivity between the at least one metallic module and the at least one ferromagnet magnetically for interfacing between the medical conduit channel and the patient conduit channel.

* * * * *